United States Patent [19]
Scarborough

[11] Patent Number: 5,866,681
[45] Date of Patent: Feb. 2, 1999

[54] THROMBIN RECEPTOR ANTAGONISTS

[75] Inventor: Robert M. Scarborough, Belmont, Calif.

[73] Assignee: COR Therapeutics, Inc., South San Francisco, Calif.

[21] Appl. No.: 407,468

[22] Filed: Mar. 20, 1995

Related U.S. Application Data

[63] Continuation of Ser. No. 80,788, Jun. 28, 1993, abandoned, which is a continuation-in-part of Ser. No. 922,340, Jul. 30, 1992, abandoned.

[51] Int. Cl.$^6$ .............................. A61K 38/04; C07K 5/00
[52] U.S. Cl. ......................... 530/326; 530/330; 530/328; 514/13; 514/18
[58] Field of Search ........................ 514/18, 13; 530/330, 530/326, 328

[56] References Cited

U.S. PATENT DOCUMENTS

| | | | |
|---|---|---|---|
| 4,859,609 | 8/1989 | Dull et al. ................................ | 436/501 |
| 5,068,222 | 11/1991 | Camble et al. ........................... | 514/15 |
| 5,256,766 | 10/1993 | Coughlin ................................. | 530/327 |
| 5,318,899 | 6/1994 | Scarborough et al. ................ | 435/69.6 |

FOREIGN PATENT DOCUMENTS

| | | |
|---|---|---|
| WO 88/03151 | 5/1988 | WIPO . |
| WO 92/14750 | 9/1992 | WIPO . |
| WO 93/18141 | 9/1993 | WIPO . |
| WO87/02882 | 10/1996 | WIPO . |

OTHER PUBLICATIONS

Coller, Barry S., et al., "Thrombin Receptor Activating Peptides: Importance of the N–Terminal Serine and Its Ionization State as Judged by pH Dependence, Nuclear Magnetic Resonance Spectroscopy, and Cleavage by Aminopeptidase M," *Biochemistry*, vol., 31, pp. 11713–11720, Jun. 1992.

Chao, Betty, et al., "Essential Groups in Synthetic Agonist Peptides for Activation of the Platelet Thrombin Receptor," *Biochemistry*, vol. 31, No. 27, pp. 6175–6178, Jul. 14, 1992.

Scarborough, R., et al., "Tethered Ligand Agonist Peptides, " *The Journal of Biological Chemistry*, vol. 267, No. 19, pp. 13146–13149, Jul. 1992.

Hollenberg, Morley, et al., "Action of Thrombin Receptor Polypeptide in Gastric Smooth Muscle: Identification of a Core Pentapeptide Retaining Full Thrombin–Mimetic Intrinsic Activity, " *Molecular Pharmacology*, vol. 42. pp. 186–197, May 1992.

Hui, Kwan Y., et al., "Minimal Sequence Requirement of Thrombin Receptor Agonist Peptide, " *Biochemical and Biophysical Research Communications*, vol., 184, No. 2, pp. 790–796, Apr. 30, 1992.

Hung, David, et al., "Cloned Platelet Thrombin Receptor is Necessary for Thrombin–induced Platelet Activation," *Journal of Clinical Investigation*, vol. 89, pp. 1350–1353, Apr. 1992.

Vassallo, R., et al., "Structure–Function Relationships in the Activation of Platelet Thrombin Receptors by Receptor–derived Peptides," *The Journal of Biological Chemistry*, vol. 267, No. 9, pp. 6081–6085, Mar. 25, 1992.

Coughlin, Shaun R., et al., "Characterization of a Functional Thrombin Receptor," *Journal of Clinical Investigation*, vol. 89, pp. 351–355, Feb. 1992.

Hung, David, et al., "Mirror Image" Antagonists of Thrombin–induced Platelet Activation Based on Thrombin Receptor Structure, *Journal of Clinical Investigation*, vol. 89, pp. 444–450, Feb. 1990.

Vouret–Craviari, V., et al., "Synthetic α–Thrombin Receptor Peptides Activate G Protein–Coupled Signaling Pathways but are Unable to Induce Mitrogenesis," *Molecular Biology of the Cell*, vol. 3, pp. 95–102, Jan. 1992.

Vu, Thien–Khai H., et al., "Domains specifying thrombin–receptor interaction," *Nature*, vol. 353, pp. 674–677, Oct. 1991.

Ngaiza, Justinian, et al., "A 14 amino acid peptide derived from the amino terminus of the cleaved thrombin receptor elevates intracellular calcium and stimulates prostacyclin production in human endothelial cells," *Biochemical and Biophysical Research Communications*, vol. 179, No. 3, pp. 1656–1661, Sep. 30, 1991.

Rasmussen, Ulla B., et al., "cDNA Cloning and Expression of a Hamster α–Thrombin Receptor Coupled to $Ca^{2+}$ Mobilization" *FEBS Letters*, vol. 288, No. 1, 2, pp. 123–128, Aug. 1991.

(List continued on next page.)

*Primary Examiner*—Cecilia J. Tsang
*Assistant Examiner*—Bennett Celsa
*Attorney, Agent, or Firm*—Townsend and Townsend and Crew LLP

[57] ABSTRACT

Peptide derivatives serving as thrombin receptor antagonists are disclosed, which bear specificity for the cellular thrombin receptor without interfering with the catalytic activities of thrombin. The derivatives generally have the formula

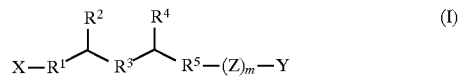

in which $R^1$ and $R^3$ are amide linkages, N-alkylamide linkages, or isosteric replacements of such linkages; $R^2$ is either a neutral amino acid side chain or a hydrophobic radical; $R^4$ is hydrophobic radical; $R^5$ is CO, $CH_2$ or SO; X is either of the formula:

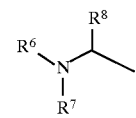

in which $R^6$ and $R^7$ are H, alkyl, cycloalkylalkyl, alkoxyalkyl, alkylthioalkyl or arylalkyl, and $R^8$ is a hydrophobic radical, or a hydrophobic residue; Y is alkoxy, hydroxy, amino, alkylamino, dialkylamino, in which any of the alkyl groups may be substituted with a basic moiety; Z is an amino acid or peptide residue; and m is zero or one.

49 Claims, No Drawings

OTHER PUBLICATIONS

Chesebro, James, et al., "Dynamic Thrombosis and Thrombolysis," *Circulation,* vol. 83, No. 5, May 1991.

Vu, Thien–Khai H., et al., "Molecular Cloning of a Functional Thrombin Receptor Reveals a Novel Proteolytic Mechanism of Receptor Activation," *Cell,* vol. 64, pp. 1057–1068, Mar. 22, 1991.

Sarembock, Ian, et al., Effectiveness of Recombinant Desulphatohirudin in Reducing Restenosis After Balloon Angioplasty of Atherosclerotic Femoral Arteries in Rabbits, *Circulation,* vol. 84, No. 1, Jul. 1991.

Chesebro, James, et al., "Role of Thrombin in Arterial Thrombosis: Implications for Therapy," *Thrombosis and Hamostasis,*vol. 66, No. 1, pp. 1–5, 1991.

Synetos, Eva, et al., "Expression of functional thrombin receptors in Xenopus oocytes injected with human endothelial cell mRNA," *Biochemical and Biophysical Research Communications,* vol. 171, No. 3, pp. 913–919, Sep. 1990.

Ruda, E.M., et al., "Structure–Activity Relationships for the Platelet Thrombin Receptor and Effects on Prostacyclin Synthesis by Human Umbilical Vein Endothelial Cells," *Biochemical Pharmacology,* vol. 39, No. 2, pp. 373–381, 1990.

Shuman, Marc, "Thrombin–Cellular Interactions," *Annals New York Academy of Sciences,* vol. 485, pp. 228–239, 1986.

Rasmussen, U.B., et al., "A Peptide Ligand of the Human Thrombin Receptor Antaganizes alpha–Thrombin and Partially Activates Platelets," *J. of Biol. Chemistry,* 268(19) :14322–14328 (5 Jul. 1993).

Ruda, E.M., et al., "Identification of Small Peptide Analogues Having Agonist and Antagonist Activity at the Platelet Thrombin Receptor," Biochemical Pharmacology, 37(12) :2417–2426 (1988).

De Caterina, R., et al., "Cellular Effects of Thrombin: Pharmacology of the Receptors in Various Call Types and Possible Development of Receptor Antagonists," Pharmacological Research, 27(1) :1–19 (Jan. 1993).

Cadroy et al., *J. Clin. Invest* 84:939–944 (1989).

Fratantoni et al., *Am J. Clin. Pathol* 94:613–617 (1990).

Hung et al., *J. Cell Biol* 116:827–832 (1992).

Jacobson et al., *J. Cell Physiol* 152:166–167 (1992).

Bar–Shavit et al., *J. Cell Biol.,* "An Arg–Gly–Asp Sequence within Thrombin Promotes Endothelial Cell Adhesion", 112:335–344 (1991).

Pipili–Synetos et al., *BBRC* 171:913–919 (1990).

Shattil et al., *J. Biol Chem* 267:18424–18431 (1992).

Spatola, In: Weinstein et al. (eds.) Chemistry and Biochemistry of Amino Acids, Peptideds and Proteins. *Marcel Dekker* Inc, New York, p. 267 (1983).

Yang et al., *Life Sci* 51:1325–1332 (1992).

Malik, Semin Thromb hemostas 12:184–196 (1986).

Walz et al., *Annals New York Academy of Sciences,* Responses of Aortic Smooth Muscle to Thrombin and Thrombine Analogues, 485:323–334 (1986).

Ruda et al., *Annals New York Academy of Sciences,* "Identification of Tripeptide Analogue (SC–40476), "That Acts as a Selective Partial Agonist–Antagonist at the Human Platelet Thrombine Receptor, 485:439–442 (1986).

Masu et al., *Nature,* "cDNA Cloning of Bovine Substance–K Receptor through oocyte Expression System", 329:836–838 (1987).

SEQUENCE LISTING ( 1 ) GENERAL INFORMATION:

( i i i ) NUMBER OF SEQUENCES: 44

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /product="OTHER"
            / note= "Xaa = preferably Arg, homoarginine, Orn, Lys,
            N-epsilon,N- epsilon-dimethyllysine, N-epsilon-
            acetimidyllysine,N-epsilon-phenylimidyllysine, Gln or
            Asn"

( i x ) FEATURE:
        ( A ) NAME/KEY: Modified-site
        ( B ) LOCATION: 2
        ( D ) OTHER INFORMATION: /product="OTHER"
            / note= "Xaa = preferably Asn, Gln, Arg, Lys,
            homoarginine, Orn,N-epsilon,N-epsilon-dimethyllysine or
            N-epsilon- methyllysine"

( i x ) FEATURE:
        ( A ) NAME/KEY: Modified-site
        ( B ) LOCATION: 3
        ( D ) OTHER INFORMATION: /product="OTHER"
            / note= "Xaa = preferably Pro, MeGly, Gly, Asp or Glu"

( i x ) FEATURE:
        ( A ) NAME/KEY: Modified-site
        ( B ) LOCATION: 4
        ( D ) OTHER INFORMATION: /product="OTHER"
            / note= "Xaa = preferably Asn, Gln, Gly or Ala"

( i x ) FEATURE:
  ( A ) NAME/KEY: Modified-site
  ( B ) LOCATION: 5
  ( D ) OTHER INFORMATION: /product="OTHER"
    / note= "Xaa = preferably Asp or Glu"

( i x ) FEATURE:
  ( A ) NAME/KEY: Modified-site
  ( B ) LOCATION: 6
  ( D ) OTHER INFORMATION: /product="OTHER"
    / note= "Xaa = preferably Lys, Arg, Orn or homoarginine"

( i x ) FEATURE:
  ( A ) NAME/KEY: Modified-site
  ( B ) LOCATION: 4..10
  ( D ) OTHER INFORMATION: /product="OTHER"
    / note= "Xaa at positions 4-10 may be present or absent,
    preferably Xaa at positions 6-10 may be present or
    absent; Xaa at positions 1-10 may be the same or
    different; Xaa at the carboxy terminus is amidated"

( x i ) SEQUENCE DESCRIPTION: SEQ ID NO:1:

Xaa  Xaa  Xaa  Xaa  Xaa  Xaa  Xaa  Xaa  Xaa  Xaa
1                   5                        1 0

( 2 ) INFORMATION FOR SEQ ID NO:2:

( i ) SEQUENCE CHARACTERISTICS:
    ( A ) LENGTH: 6 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( A ) NAME/KEY: Modified-site
    ( B ) LOCATION: 2
    ( D ) OTHER INFORMATION: /product="OTHER"
      / note= "Xaa = Lys, Arg or homoarginine"

( i x ) FEATURE:
    ( A ) NAME/KEY: Modified-site
    ( B ) LOCATION: 3..6
    ( D ) OTHER INFORMATION: /product="OTHER"
      / note= "Xaa at positions 3-6 may be present or absent;
      Xaa at the carboxy terminus is amidated"

( x i ) SEQUENCE DESCRIPTION: SEQ ID NO:2:

Arg  Xaa  Xaa  Xaa  Xaa  Xaa
1                   5

( 2 ) INFORMATION FOR SEQ ID NO:3:

( i ) SEQUENCE CHARACTERISTICS:
    ( A ) LENGTH: 6 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( A ) NAME/KEY: Modified-site
    ( B ) LOCATION: 3..6
    ( D ) OTHER INFORMATION: /product="OTHER"
      / note= "Xaa at positions 3-6 may be present or absent;
      Xaa at the carboxyl terminus is amidated"

( x i ) SEQUENCE DESCRIPTION: SEQ ID NO:3:

Xaa  Xaa  Xaa  Xaa  Xaa  Xaa
1                   5

( 2 ) INFORMATION FOR SEQ ID NO:4:

( i ) SEQUENCE CHARACTERISTICS:
  ( A ) LENGTH: 5 amino acids
  ( B ) TYPE: amino acid
  ( C ) STRANDEDNESS:
  ( D ) TOPOLOGY: linear ( i i ) MOLECULE TYPE: peptide ( i x ) FEATURE:
  ( A ) NAME/KEY: Modified-site
  ( B ) LOCATION: 1
  ( D ) OTHER INFORMATION: /product="OTHER"
    / note= "Xaa = N,N-di-n-pentylphenylalanine"

( i x ) FEATURE:
  ( A ) NAME/KEY: Modified-site
  ( B ) LOCATION: 2
  ( D ) OTHER INFORMATION: /product="OTHER"
    / note= "Xaa = cyclohexylalanine"

( i x ) FEATURE:
  ( A ) NAME/KEY: Modified-site
  ( B ) LOCATION: 3
  ( D ) OTHER INFORMATION: /product="OTHER"
    / note= "Xaa = cyclohexylalanine"

( i x ) FEATURE:
  ( A ) NAME/KEY: Modified-site
  ( B ) LOCATION: 5
  ( D ) OTHER INFORMATION: /product="OTHER"
    / note= "Xaa = lysinamide"

( x i ) SEQUENCE DESCRIPTION: SEQ ID NO:4:

Xaa Xaa Xaa Arg Xaa
1        5

( 2 ) INFORMATION FOR SEQ ID NO:5:

( i ) SEQUENCE CHARACTERISTICS:
  ( A ) LENGTH: 4 amino acids
  ( B ) TYPE: amino acid
  ( C ) STRANDEDNESS:
  ( D ) TOPOLOGY: linear ( i i ) MOLECULE TYPE: peptide ( i x ) FEATURE:
  ( A ) NAME/KEY: Modified-site
  ( B ) LOCATION: 1
  ( D ) OTHER INFORMATION: /product="OTHER"
    / note= "Xaa = 2-phenoxybutyrylcyclohexylalanine"

( i x ) FEATURE:
  ( A ) NAME/KEY: Modified-site
  ( B ) LOCATION: 2
  ( D ) OTHER INFORMATION: /product="OTHER"
    / note= "Xaa = cyclohexylalanine"

( i x ) FEATURE:
  ( A ) NAME/KEY: Modified-site
  ( B ) LOCATION: 4
  ( D ) OTHER INFORMATION: /product="OTHER"
    / note= "Xaa = lysinamide"

( x i ) SEQUENCE DESCRIPTION: SEQ ID NO:5:

Xaa Xaa Arg Xaa
1

( 2 ) INFORMATION FOR SEQ ID NO:6:

( i ) SEQUENCE CHARACTERISTICS:
  ( A ) LENGTH: 4 amino acids
  ( B ) TYPE: amino acid
  ( C ) STRANDEDNESS:
  ( D ) TOPOLOGY: linear (ii) MOLECULE TYPE: peptide (ix) FEATURE:
  (A) NAME/KEY: Modified-site
  (B) LOCATION: 1
  (D) OTHER INFORMATION: /product="OTHER"
      /note= "Xaa = cyclohexylalanine"

(ix) FEATURE:
  (A) NAME/KEY: Modified-site
  (B) LOCATION: 2
  (D) OTHER INFORMATION: /product="OTHER"
      /note= "Xaa = cyclohexylalanine"

(ix) FEATURE:
  (A) NAME/KEY: Modified-site
  (B) LOCATION: 4
  (D) OTHER INFORMATION: /product="OTHER"
      /note= "Xaa = lysine coupled to p-methylbenzhydrylamine
      HCl (MBHA) resin"

(xi) SEQUENCE DESCRIPTION: SEQ ID NO:6:

Xaa Xaa Arg Xaa
1

(2) INFORMATION FOR SEQ ID NO:7:

(i) SEQUENCE CHARACTERISTICS:
    (A) LENGTH: 5 amino acids
    (B) TYPE: amino acid
    (C) STRANDEDNESS:
    (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /product="OTHER"
        /note= "N-n-pentyl-1,2,3,4-tetrahydroisoquinoline-3
        - carboxylic acid"

(ix) FEATURE:
    (A) NAME/KEY: Modified-site
    (B) LOCATION: 2
    (D) OTHER INFORMATION: /product="OTHER"
        /note= "Xaa = cyclohexylalanine"

(ix) FEATURE:
    (A) NAME/KEY: Modified-site
    (B) LOCATION: 3
    (D) OTHER INFORMATION: /product="OTHER"
        /note= "Xaa = cyclohexylalanine"

(ix) FEATURE:
    (A) NAME/KEY: Modified-site
    (B) LOCATION: 5
    (D) OTHER INFORMATION: /product="OTHER"
        /note= "Xaa = lysinamide"

(xi) SEQUENCE DESCRIPTION: SEQ ID NO:7:

Xaa Xaa Xaa Arg Xaa
1                 5

(2) INFORMATION FOR SEQ ID NO:8:

(i) SEQUENCE CHARACTERISTICS:
    (A) LENGTH: 5 amino acids
    (B) TYPE: amino acid
    (C) STRANDEDNESS:
    (D) TOPOLOGY: linear (ii) MOLECULE TYPE: peptide (ix) FEATURE:

(A) NAME/KEY: Modified-site
(B) LOCATION: 1
(D) OTHER INFORMATION: /product="OTHER"
/ note= "Xaa = 1,2,3,4-tetrahydroisoquinoline-3-
carboxylic acid"

(ix) FEATURE:
(A) NAME/KEY: Modified-site
(B) LOCATION: 2
(D) OTHER INFORMATION: /product="OTHER"
/ note= "Xaa = cyclohexylalanine"

(ix) FEATURE:
(A) NAME/KEY: Modified-site
(B) LOCATION: 3
(D) OTHER INFORMATION: /product="OTHER"
/ note= "Xaa = cyclohexylalanine"

(ix) FEATURE:
(A) NAME/KEY: Modified-site
(B) LOCATION: 5
(D) OTHER INFORMATION: /product="OTHER"
/ note= "Xaa = lysine coupled to p-methylbenzhydrylamine
HCl (MBHA) resin"

(xi) SEQUENCE DESCRIPTION: SEQ ID NO:8:

Xaa  Xaa  Xaa  Arg  Xaa
1                    5

(2) INFORMATION FOR SEQ ID NO:9:

(i) SEQUENCE CHARACTERISTICS:
(A) LENGTH: 4 amino acids
(B) TYPE: amino acid
(C) STRANDEDNESS:
(D) TOPOLOGY: linear (ii) MOLECULE TYPE: peptide (ix) FEATURE:
(A) NAME/KEY: Modified-site
(B) LOCATION: 1
(D) OTHER INFORMATION: /product="OTHER"
/ note= "Xaa = N-[2-(hexyl)-styryl]-cyclohexylalanine"

(ix) FEATURE:
(A) NAME/KEY: Modified-site
(B) LOCATION: 2
(D) OTHER INFORMATION: /product="OTHER"
/ note= "Xaa = cyclohexylalanine"

(ix) FEATURE:
(A) NAME/KEY: Modified-site
(B) LOCATION: 4
(D) OTHER INFORMATION: /product="OTHER"
/ note= "Xaa = lysinamide"

(xi) SEQUENCE DESCRIPTION: SEQ ID NO:9:

Xaa  Xaa  Arg  Xaa
1

(2) INFORMATION FOR SEQ ID NO:10:

(i) SEQUENCE CHARACTERISTICS:
(A) LENGTH: 4 amino acids
(B) TYPE: amino acid
(C) STRANDEDNESS:
(D) TOPOLOGY: linear (ii) MOLECULE TYPE: peptide (ix) FEATURE:
(A) NAME/KEY: Modified-site
(B) LOCATION: 1
(D) OTHER INFORMATION: /product="OTHER"
/ note= "Xaa = cyclohexylalanine trifluoroacetate"

( i x ) FEATURE:
    ( A ) NAME/KEY: Modified-site
    ( B ) LOCATION: 2
    ( D ) OTHER INFORMATION: /product="OTHER"
        / note= "Xaa = cyclohexylalanine"

( i x ) FEATURE:
    ( A ) NAME/KEY: Modified-site
    ( B ) LOCATION: 4
    ( D ) OTHER INFORMATION: /product="OTHER"
        / note= "Xaa = lysine coupled to p-methylbenzhydrylamine HCl (MBHA) resin"

( x i ) SEQUENCE DESCRIPTION: SEQ ID NO:10:

Xaa Xaa Arg Xaa
1

( 2 ) INFORMATION FOR SEQ ID NO:11:

( i ) SEQUENCE CHARACTERISTICS:
    ( A ) LENGTH: 9 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /product="OTHER"
        / note= "Xaa = Phe N-substituted with various R groups"

( i x ) FEATURE:
    ( A ) NAME/KEY: Modified-site
    ( B ) LOCATION: 2
    ( D ) OTHER INFORMATION: /product="OTHER"
        / note= "Xaa = cyclohexylalanine"

( i x ) FEATURE:
    ( A ) NAME/KEY: Modified-site
    ( B ) LOCATION: 3
    ( D ) OTHER INFORMATION: /product="OTHER"
        / note= "Xaa = cyclohexylalanine"

( i x ) FEATURE:
    ( A ) NAME/KEY: Modified-site
    ( B ) LOCATION: 9
    ( D ) OTHER INFORMATION: /product="OTHER"
        / note= "Xaa = lysinamide"

( x i ) SEQUENCE DESCRIPTION: SEQ ID NO:11:

Xaa Xaa Xaa Arg Lys Pro Asn Asp Xaa
1                  5

( 2 ) INFORMATION FOR SEQ ID NO:12:

( i ) SEQUENCE CHARACTERISTICS:
    ( A ) LENGTH: 5 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /product="OTHER"
        / note= "Xaa = N-n-pentylphenethylalanine"

( i x ) FEATURE:
    ( A ) NAME/KEY: Modified-site
    ( B ) LOCATION: 2
    ( D ) OTHER INFORMATION: /product="OTHER"
        / note= "Xaa = cyclohexylalanine"

( i x ) FEATURE:
    ( A ) NAME/KEY: Modified-site
    ( B ) LOCATION: 3
    ( D ) OTHER INFORMATION: /product="OTHER"
        / note= "Xaa = cyclohexylalanine"

( i x ) FEATURE:
    ( A ) NAME/KEY: Modified-site
    ( B ) LOCATION: 5
    ( D ) OTHER INFORMATION: /product="OTHER"
        / note= "Xaa = lysinamide"

( x i ) SEQUENCE DESCRIPTION: SEQ ID NO:12:

Xaa Xaa Xaa Arg Xaa
1                   5

( 2 ) INFORMATION FOR SEQ ID NO:13:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /product="OTHER"
            / note= "Xaa =
            N- methylenecyclohexyl-1,2,3,4-tetrahydroisoquinoline-3
            - carboxylic acid"

( i x ) FEATURE:
        ( A ) NAME/KEY: Modified-site
        ( B ) LOCATION: 2
        ( D ) OTHER INFORMATION: /product="OTHER"
            / note= "Xaa = cyclohexylalanine"

( i x ) FEATURE:
        ( A ) NAME/KEY: Modified-site
        ( B ) LOCATION: 3
        ( D ) OTHER INFORMATION: /product="OTHER"
            / note= "Xaa = cyclohexylalanine"

( i x ) FEATURE:
        ( A ) NAME/KEY: Modified-site
        ( B ) LOCATION: 5
        ( D ) OTHER INFORMATION: /product="OTHER"
            / note= "Xaa = lysinamide"

( x i ) SEQUENCE DESCRIPTION: SEQ ID NO:13:

Xaa Xaa Xaa Arg Xaa
1                   5

( 2 ) INFORMATION FOR SEQ ID NO:14:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /product="OTHER"
            / note= "Xaa =
            N-neopentyl- 1,2,3,4-tetrahydroisoquinoline-3-carboxylic
            acid"

( i x ) FEATURE:

(A) NAME/KEY: Modified-site
(B) LOCATION: 2
(D) OTHER INFORMATION: /product="OTHER"
/ note= "Xaa = cyclohexylalanine"

( i x ) FEATURE:
(A) NAME/KEY: Modified-site
(B) LOCATION: 3
(D) OTHER INFORMATION: /product="OTHER"
/ note= "Xaa = cyclohexylalanine"

( i x ) FEATURE:
(A) NAME/KEY: Modified-site
(B) LOCATION: 5
(D) OTHER INFORMATION: /product="OTHER"
/ note= "Xaa = lysinamide"

( x i ) SEQUENCE DESCRIPTION: SEQ ID NO:14:

Xaa Xaa Xaa Arg Xaa
1               5

( 2 ) INFORMATION FOR SEQ ID NO:15:

( i ) SEQUENCE CHARACTERISTICS:
(A) LENGTH: 5 amino acids
(B) TYPE: amino acid
(C) STRANDEDNESS:
(D) TOPOLOGY: linear ( i i ) MOLECULE TYPE: peptide ( i x ) FEATURE:
(A) NAME/KEY: Modified-site
(B) LOCATION: 1
(D) OTHER INFORMATION: /product="OTHER"
/ note= "Xaa = N-n-pentylphenylalanine"

( i x ) FEATURE:
(A) NAME/KEY: Modified-site
(B) LOCATION: 2
(D) OTHER INFORMATION: /product="OTHER"
/ note= "Xaa = cyclohexylalanine"

( i x ) FEATURE:
(A) NAME/KEY: Modified-site
(B) LOCATION: 3
(D) OTHER INFORMATION: /product="OTHER"
/ note= "Xaa = cyclohexylalanine"

( i x ) FEATURE:
(A) NAME/KEY: Modified-site
(B) LOCATION: 5
(D) OTHER INFORMATION: /product="OTHER"
/ note= "Xaa = lysinamide"

( x i ) SEQUENCE DESCRIPTION: SEQ ID NO:15:

Xaa Xaa Xaa Arg Xaa
1               5

( 2 ) INFORMATION FOR SEQ ID NO:16:

( i ) SEQUENCE CHARACTERISTICS:
(A) LENGTH: 5 amino acids
(B) TYPE: amino acid
(C) STRANDEDNESS:
(D) TOPOLOGY: linear ( i i ) MOLECULE TYPE: peptide ( i x ) FEATURE:
(A) NAME/KEY: Modified-site
(B) LOCATION: 1
(D) OTHER INFORMATION: /product="OTHER"
/ note= "Xaa = N-n-pentyl-N-methylphenylalanine"

( i x ) FEATURE:

(A) NAME/KEY: Modified-site
(B) LOCATION: 2
(D) OTHER INFORMATION: /product="OTHER"
/ note= "Xaa = cyclohexylalanine"

(ix) FEATURE:
(A) NAME/KEY: Modified-site
(B) LOCATION: 3
(D) OTHER INFORMATION: /product="OTHER"
/ note= "Xaa = cyclohexylalanine"

(ix) FEATURE:
(A) NAME/KEY: Modified-site
(B) LOCATION: 5
(D) OTHER INFORMATION: /product="OTHER"
/ note= "Xaa = lysinamide"

(xi) SEQUENCE DESCRIPTION: SEQ ID NO:16:

Xaa Xaa Xaa Arg Xaa
1               5

(2) INFORMATION FOR SEQ ID NO:17:

(i) SEQUENCE CHARACTERISTICS:
(A) LENGTH: 5 amino acids
(B) TYPE: amino acid
(C) STRANDEDNESS:
(D) TOPOLOGY: linear (ii) MOLECULE TYPE: peptide (ix) FEATURE:
(A) NAME/KEY: Modified-site
(B) LOCATION: 1
(D) OTHER INFORMATION: /product="OTHER"
/ note= "Xaa = N-methylphenylalanine with various N - substituted R groups"

(ix) FEATURE:
(A) NAME/KEY: Modified-site
(B) LOCATION: 2
(D) OTHER INFORMATION: /product="OTHER"
/ note= "Xaa = cyclohexylalanine"

(ix) FEATURE:
(A) NAME/KEY: Modified-site
(B) LOCATION: 3
(D) OTHER INFORMATION: /product="OTHER"
/ note= "Xaa = cyclohexylalanine"

(ix) FEATURE:
(A) NAME/KEY: Modified-site
(B) LOCATION: 5
(D) OTHER INFORMATION: /product="OTHER"
/ note= "Xaa = lysinamide"

(xi) SEQUENCE DESCRIPTION: SEQ ID NO:17:

Xaa Xaa Xaa Arg Xaa
1               5

(2) INFORMATION FOR SEQ ID NO:18:

(i) SEQUENCE CHARACTERISTICS:
(A) LENGTH: 4 amino acids
(B) TYPE: amino acid
(C) STRANDEDNESS:
(D) TOPOLOGY: linear (ii) MOLECULE TYPE: peptide (ix) FEATURE:
(A) NAME/KEY: Modified-site
(B) LOCATION: 1
(D) OTHER INFORMATION: /product="OTHER"
/ note= "Xaa = cyclohexylalanine with various N - substituted R groups"

( i x ) FEATURE:
     ( A ) NAME/KEY: Modified-site
     ( B ) LOCATION: 2
     ( D ) OTHER INFORMATION: /product="OTHER"
          / note= "Xaa = cyclohexylalanine"

( i x ) FEATURE:
     ( A ) NAME/KEY: Modified-site
     ( B ) LOCATION: 4
     ( D ) OTHER INFORMATION: /product="OTHER"
          / note= "Xaa = lysinamide"

( x i ) SEQUENCE DESCRIPTION: SEQ ID NO:18:

Xaa  Xaa  Arg  Xaa
  1

( 2 ) INFORMATION FOR SEQ ID NO:19:

( i ) SEQUENCE CHARACTERISTICS:
       ( A ) LENGTH: 5 amino acids
       ( B ) TYPE: amino acid
       ( C ) STRANDEDNESS:
       ( D ) TOPOLOGY: linear ( i i ) MOLECULE TYPE: peptide ( i x ) FEATURE:
       ( A ) NAME/KEY: Modified-site
       ( B ) LOCATION: 1
       ( D ) OTHER INFORMATION: /product="OTHER"
            / note= "Xaa =
              N-n-pentyl- 1,2,3,4-tetrahydroisoquinoline-3-carboxylic
              acid"

( i x ) FEATURE:
       ( A ) NAME/KEY: Modified-site
       ( B ) LOCATION: 2
       ( D ) OTHER INFORMATION: /product="OTHER"
            / note= "Xaa = cyclohexylalanine"

( i x ) FEATURE:
       ( A ) NAME/KEY: Modified-site
       ( B ) LOCATION: 3
       ( D ) OTHER INFORMATION: /product="OTHER"
            / note= "Xaa = cyclohexylalanine"

( i x ) FEATURE:
       ( A ) NAME/KEY: Modified-site
       ( B ) LOCATION: 4
       ( D ) OTHER INFORMATION: /product="OTHER"
            / note= "Xaa = N-alpha-methylarginine"

( i x ) FEATURE:
       ( A ) NAME/KEY: Modified-site
       ( B ) LOCATION: 5
       ( D ) OTHER INFORMATION: /product="OTHER"
            / note= "Xaa = argininamide"

( x i ) SEQUENCE DESCRIPTION: SEQ ID NO:19:

Xaa  Xaa  Xaa  Xaa  Xaa
  1                      5

( 2 ) INFORMATION FOR SEQ ID NO:20:

( i ) SEQUENCE CHARACTERISTICS:
       ( A ) LENGTH: 4 amino acids
       ( B ) TYPE: amino acid
       ( C ) STRANDEDNESS:
       ( D ) TOPOLOGY: linear ( i i ) MOLECULE TYPE: peptide ( i x ) FEATURE:
       ( A ) NAME/KEY: Modified-site
       ( B ) LOCATION: 1

(D) OTHER INFORMATION: /product="OTHER"
/ note= "Xaa =
N-n-pentyl- 1,2,3,4-tetrahydroisoquinoline-3-carboxylic
acid"

(ix) FEATURE:
(A) NAME/KEY: Modified-site
(B) LOCATION: 2
(D) OTHER INFORMATION: /product="OTHER"
/ note= "Xaa = cyclohexylalanine"

(ix) FEATURE:
(A) NAME/KEY: Modified-site
(B) LOCATION: 3
(D) OTHER INFORMATION: /product="OTHER"
/ note= "Xaa = cyclohexylalanine"

(ix) FEATURE:
(A) NAME/KEY: Modified-site
(B) LOCATION: 4
(D) OTHER INFORMATION: /product="OTHER"
/ note= "Xaa = N-alpha-methylargininamide"

(xi) SEQUENCE DESCRIPTION: SEQ ID NO:20:

Xaa Xaa Xaa Xaa
1

(2) INFORMATION FOR SEQ ID NO:21:

(i) SEQUENCE CHARACTERISTICS:
(A) LENGTH: 7 amino acids
(B) TYPE: amino acid
(C) STRANDEDNESS:
(D) TOPOLOGY: linear (ii) MOLECULE TYPE: peptide (ix) FEATURE:
(A) NAME/KEY: Modified-site
(B) LOCATION: 1
(D) OTHER INFORMATION: /product="OTHER"
/ note= "Xaa =
N-neopentyl- 1,2,3,4-tetrahydroisoquinoline-3-carboxylic
acid"

(ix) FEATURE:
(A) NAME/KEY: Modified-site
(B) LOCATION: 2
(D) OTHER INFORMATION: /product="OTHER"
/ note= "Xaa = cyclohexylalanine"

(ix) FEATURE:
(A) NAME/KEY: Modified-site
(B) LOCATION: 3
(D) OTHER INFORMATION: /product="OTHER"
/ note= "Xaa = cyclohexylalanine"

(xi) SEQUENCE DESCRIPTION: SEQ ID NO:21:

Xaa Xaa Xaa Arg Lys Asp Lys
1               5

(2) INFORMATION FOR SEQ ID NO:22:

(i) SEQUENCE CHARACTERISTICS:
(A) LENGTH: 4 amino acids
(B) TYPE: amino acid
(C) STRANDEDNESS:
(D) TOPOLOGY: linear (ii) MOLECULE TYPE: peptide (ix) FEATURE:
(A) NAME/KEY: Modified-site
(B) LOCATION: 1
(D) OTHER INFORMATION: /product="OTHER"
/ note= "Xaa = 2-phenoxybutyrylphenylalanine"

( i x ) FEATURE:
    ( A ) NAME/KEY: Modified-site
    ( B ) LOCATION: 2
    ( D ) OTHER INFORMATION: /product="OTHER"
       / note= "Xaa = cyclohexylalanine"

( i x ) FEATURE:
    ( A ) NAME/KEY: Modified-site
    ( B ) LOCATION: 4
    ( D ) OTHER INFORMATION: /product="OTHER"
       / note= "Xaa = lysinamide"

( x i ) SEQUENCE DESCRIPTION: SEQ ID NO:22:

Xaa Xaa Arg Xaa
1

( 2 ) INFORMATION FOR SEQ ID NO:23:

( i ) SEQUENCE CHARACTERISTICS:
    ( A ) LENGTH: 4 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /product="OTHER"
       / note= "Xaa = 2-phenoxybutyrylcyclohexylalanine"

( i x ) FEATURE:
    ( A ) NAME/KEY: Modified-site
    ( B ) LOCATION: 2
    ( D ) OTHER INFORMATION: /product="OTHER"
       / note= "Xaa = cyclohexylalanine"

( i x ) FEATURE:
    ( A ) NAME/KEY: Modified-site
    ( B ) LOCATION: 3
    ( D ) OTHER INFORMATION: /product="OTHER"
       / note= "Xaa = homoarginine"

( i x ) FEATURE:
    ( A ) NAME/KEY: Modified-site
    ( B ) LOCATION: 4
    ( D ) OTHER INFORMATION: /product="OTHER"
       / note= "Xaa = lysinamide"

( x i ) SEQUENCE DESCRIPTION: SEQ ID NO:23:

Xaa Xaa Xaa Xaa
1

( 2 ) INFORMATION FOR SEQ ID NO:24:

( i ) SEQUENCE CHARACTERISTICS:
    ( A ) LENGTH: 4 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /product="OTHER"
       / note= "Xaa = 2-phenoxybutyrylcyclohexylalanine"

( i x ) FEATURE:
    ( A ) NAME/KEY: Modified-site
    ( B ) LOCATION: 2
    ( D ) OTHER INFORMATION: /product="OTHER"
       / note= "Xaa = cyclohexylalanine"

(ix) FEATURE:
  (A) NAME/KEY: Modified-site
  (B) LOCATION: 4
  (D) OTHER INFORMATION: /product="OTHER"
    /note= "Xaa = ornithinamide"

(xi) SEQUENCE DESCRIPTION: SEQ ID NO:24:

Xaa Xaa Arg Xaa
1

(2) INFORMATION FOR SEQ ID NO:25:

(i) SEQUENCE CHARACTERISTICS:
    (A) LENGTH: 4 amino acids
    (B) TYPE: amino acid
    (C) STRANDEDNESS:
    (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /product="OTHER"
      /note= "Xaa = 2-phenoxybutyrylcyclohexylalanine"

(ix) FEATURE:
    (A) NAME/KEY: Modified-site
    (B) LOCATION: 2
    (D) OTHER INFORMATION: /product="OTHER"
      /note= "Xaa = cyclohexylalanine"

(ix) FEATURE:
    (A) NAME/KEY: Modified-site
    (B) LOCATION: 4
    (D) OTHER INFORMATION: /product="OTHER"
      /note= "Xaa = lysinamide"

(xi) SEQUENCE DESCRIPTION: SEQ ID NO:25:

Xaa Xaa Lys Xaa
1

(2) INFORMATION FOR SEQ ID NO:26:

(i) SEQUENCE CHARACTERISTICS:
    (A) LENGTH: 4 amino acids
    (B) TYPE: amino acid
    (C) STRANDEDNESS:
    (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /product="OTHER"
      /note= "Xaa = 2-phenoxybutyrylcyclohexylalanine"

(ix) FEATURE:
    (A) NAME/KEY: Modified-site
    (B) LOCATION: 2
    (D) OTHER INFORMATION: /product="OTHER"
      /note= "Xaa = cyclohexylalanine"

(ix) FEATURE:
    (A) NAME/KEY: Modified-site
    (B) LOCATION: 3
    (D) OTHER INFORMATION: /product="Orn"

(ix) FEATURE:
    (A) NAME/KEY: Modified-site
    (B) LOCATION: 4
    (D) OTHER INFORMATION: /product="OTHER"
      /note= "Xaa = lysinamide"

( x i ) SEQUENCE DESCRIPTION: SEQ ID NO:26:

Xaa Xaa Xaa Xaa
1

( 2 ) INFORMATION FOR SEQ ID NO:27:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /product="OTHER"
        / note= "Xaa = 2-phenoxybutyrylcyclohexylalanine"

( i x ) FEATURE:
        ( A ) NAME/KEY: Modified-site
        ( B ) LOCATION: 2
        ( D ) OTHER INFORMATION: /product="OTHER"
        / note= "Xaa = cyclohexylalanine"

( i x ) FEATURE:
        ( A ) NAME/KEY: Modified-site
        ( B ) LOCATION: 4
        ( D ) OTHER INFORMATION: /product="OTHER"
        / note= "Xaa = argininamide"

( x i ) SEQUENCE DESCRIPTION: SEQ ID NO:27:

Xaa Xaa Arg Xaa
1

( 2 ) INFORMATION FOR SEQ ID NO:28:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /product="OTHER"
        / note= "Xaa = 2-phenoxybutyrylcyclohexylalanine"

( i x ) FEATURE:
        ( A ) NAME/KEY: Modified-site
        ( B ) LOCATION: 2
        ( D ) OTHER INFORMATION: /product="OTHER"
        / note= "Xaa = cyclohexylalanine"

( i x ) FEATURE:
        ( A ) NAME/KEY: Modified-site
        ( B ) LOCATION: 3
        ( D ) OTHER INFORMATION: /product="OTHER"
        / note= "Xaa = N-alpha-methylarginine"

( i x ) FEATURE:
        ( A ) NAME/KEY: Modified-site
        ( B ) LOCATION: 4
        ( D ) OTHER INFORMATION: /product="OTHER"
        / note= "Xaa = lysinamide"

( x i ) SEQUENCE DESCRIPTION: SEQ ID NO:28:

Xaa Xaa Xaa Xaa
1

( 2 ) INFORMATION FOR SEQ ID NO:29:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /product="OTHER"
            / note= "Xaa = 2-phenoxybutyrylcyclohexylalanine"

( i x ) FEATURE:
        ( A ) NAME/KEY: Modified-site
        ( B ) LOCATION: 2
        ( D ) OTHER INFORMATION: /product="OTHER"
            / note= "Xaa = cyclohexylalanine"

( i x ) FEATURE:
        ( A ) NAME/KEY: Modified-site
        ( B ) LOCATION: 3
        ( D ) OTHER INFORMATION: /product="OTHER"
            / note= "Xaa = N-alpha-methylarginine"

( i x ) FEATURE:
        ( A ) NAME/KEY: Modified-site
        ( B ) LOCATION: 4
        ( D ) OTHER INFORMATION: /product="OTHER"
            / note= "Xaa = argininamide"

( x i ) SEQUENCE DESCRIPTION: SEQ ID NO:29:

Xaa    Xaa    Xaa    Xaa
    1

( 2 ) INFORMATION FOR SEQ ID NO:30:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /product="OTHER"
            / note= "Xaa = 2-phenoxybutyrylcyclohexylalanine"

( i x ) FEATURE:
        ( A ) NAME/KEY: Modified-site
        ( B ) LOCATION: 2
        ( D ) OTHER INFORMATION: /product="OTHER"
            / note= "Xaa = cyclohexylalanine"

( i x ) FEATURE:
        ( A ) NAME/KEY: Modified-site
        ( B ) LOCATION: 3
        ( D ) OTHER INFORMATION: /product="OTHER"
            / note= "Xaa = homoarginine"

( i x ) FEATURE:
        ( A ) NAME/KEY: Modified-site
        ( B ) LOCATION: 4
        ( D ) OTHER INFORMATION: /product="OTHER"
            / note= "Xaa = argininamide"

( x i ) SEQUENCE DESCRIPTION: SEQ ID NO:30:

Xaa    Xaa    Xaa    Xaa
    1

( 2 ) INFORMATION FOR SEQ ID NO:31:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /product="OTHER"
            / note= "Xaa = 2-phenoxybutyrylphenylalanine"

( i x ) FEATURE:
        ( A ) NAME/KEY: Modified-site
        ( B ) LOCATION: 2
        ( D ) OTHER INFORMATION: /product="OTHER"
            / note= "Xaa = cyclohexylalanine"

( i x ) FEATURE:
        ( A ) NAME/KEY: Modified-site
        ( B ) LOCATION: 3
        ( D ) OTHER INFORMATION: /product="OTHER"
            / note= "Xaa = homoarginine"

( i x ) FEATURE:
        ( A ) NAME/KEY: Modified-site
        ( B ) LOCATION: 4
        ( D ) OTHER INFORMATION: /product="OTHER"
            / note= "Xaa = argininamide"

( x i ) SEQUENCE DESCRIPTION: SEQ ID NO:31:

Xaa  Xaa  Xaa  Xaa
    1

( 2 ) INFORMATION FOR SEQ ID NO:32:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 3..20
        ( D ) OTHER INFORMATION: /product="OTHER"
            / note= "Xaa at positions 3-20 may be present or absent"

( x i ) SEQUENCE DESCRIPTION: SEQ ID NO:32:

Xaa  Xaa  Xaa  Xaa  Xaa  Xaa  Xaa  Xaa  Xaa  Xaa  Xaa  Xaa  Xaa  Xaa  Xaa  Xaa
    1                5                        10                       15

Xaa  Xaa  Xaa  Xaa
                  20

( 2 ) INFORMATION FOR SEQ ID NO:33:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /product="OTHER"
            / note= "Xaa = Arg, homoarginine, Orn, Lys, N-epsilon,N- epsilon-dimethyllysine, N-epsilon
- acetimidyllysine,N-epsilon-phenylimidyllysine, Gln or
Asn"

( i x ) FEATURE:
    ( A ) NAME/KEY: Modified-site
    ( B ) LOCATION: 3..10
    ( D ) OTHER INFORMATION: /product="OTHER"
        / note= "Xaa at positions 3-10 may be present or absent"

( x i ) SEQUENCE DESCRIPTION: SEQ ID NO:33:

Xaa  Xaa  Xaa  Xaa  Xaa  Xaa  Xaa  Xaa  Xaa  Xaa
1                            5                                1 0

( 2 ) INFORMATION FOR SEQ ID NO:34:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /product="OTHER"
            / note= "Xaa = Arg, homoarginine, Orn, Lys,
            N-epsilon,N- epsilon-dimethyllysine, N-epsilon
            - acetimidyllysine,N-epsilon-phenimidyllysine, Gln or
            Asn"

( i x ) FEATURE:
        ( A ) NAME/KEY: Modified-site
        ( B ) LOCATION: 2
        ( D ) OTHER INFORMATION: /product="OTHER"
            / note= "Xaa = Asn, Gln, Arg, Lys, homoarginine, Orn,
            N-epsilon,N- epsilon-dimethyllysine or N-epsilon
            - methyllysine"

( i x ) FEATURE:
        ( A ) NAME/KEY: Modified-site
        ( B ) LOCATION: 3..10
        ( D ) OTHER INFORMATION: /product="OTHER"
            / note= "Xaa at positions 3-10 may be present or absent"

( x i ) SEQUENCE DESCRIPTION: SEQ ID NO:34:

Xaa  Xaa  Xaa  Xaa  Xaa  Xaa  Xaa  Xaa  Xaa  Xaa
1                            5                                1 0

( 2 ) INFORMATION FOR SEQ ID NO:35:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /product="OTHER"
            / note= "Xaa = Arg, homoarginine, Orn, Lys,
            N-epsilon,N- epsilon-dimethyllysine, N-epsilon
            - acetimidyllysine,N-epsilon-phenylimidyllysine, Gln or
            Asn"

( i x ) FEATURE:
        ( A ) NAME/KEY: Modified-site
        ( B ) LOCATION: 2
        ( D ) OTHER INFORMATION: /product="OTHER"
            / note= "Xaa = Asn, Gln, Arg, Lys, homoarginine, Orn,
            N-epsilon,N- epsilon-dimethyllysine or N-epsilon -methyllysine"

(ix) FEATURE:
    (A) NAME/KEY: Modified-site
    (B) LOCATION: 3
    (D) OTHER INFORMATION: /product="OTHER"
        / note= "Xaa = Pro, MeGly, Gly, Asp or Glu"

(ix) FEATURE:
    (A) NAME/KEY: Modified-site
    (B) LOCATION: 4..10
    (D) OTHER INFORMATION: /product="OTHER"
        / note= "Xaa at positions 4-10 may be present or absent"

(xi) SEQUENCE DESCRIPTION: SEQ ID NO:35:

Xaa Xaa Xaa Xaa Xaa Xaa Xaa Xaa Xaa Xaa
1               5                       10

(2) INFORMATION FOR SEQ ID NO:36:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product="OTHER"
            / note= "Xaa = Arg, homoarginine, Orn, Lys,
            N-epsilon,N- epsilon-dimethyllysine, N-epsilon
            - acetimidyllysine,N-epsilon-phenylimidyllysine, Gln or
            Asn"

(ix) FEATURE:
        (A) NAME/KEY: Modified-site
        (B) LOCATION: 2
        (D) OTHER INFORMATION: /product="OTHER"
            / note= "Xaa = Asn, Gln, Arg, Lys, homoarginine, Orn,
            N-epsilon,N- epsilon-dimethyllysine or N-epsilon
            - methyllysine"

(ix) FEATURE:
        (A) NAME/KEY: Modified-site
        (B) LOCATION: 3
        (D) OTHER INFORMATION: /product="OTHER"
            / note= "Xaa = Pro, MeGly, Gly, Asp or Glu"

(ix) FEATURE:
        (A) NAME/KEY: Modified-site
        (B) LOCATION: 4
        (D) OTHER INFORMATION: /product="OTHER"
            / note= "Xaa = Asn, Gln, Gly or Ala"

(ix) FEATURE:
        (A) NAME/KEY: Modified-site
        (B) LOCATION: 5..10
        (D) OTHER INFORMATION: /product="OTHER"
            / note= "Xaa at positions 5-10 may be present or absent"

(xi) SEQUENCE DESCRIPTION: SEQ ID NO:36:

Xaa Xaa Xaa Xaa Xaa Xaa Xaa Xaa Xaa Xaa
1               5                       10

(2) INFORMATION FOR SEQ ID NO:37:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide ( i x ) FEATURE:
 ( A ) NAME/KEY: Modified-site
 ( B ) LOCATION: 1
 ( D ) OTHER INFORMATION: /product="OTHER"
  / note= "Xaa = Arg, homoarginine, Orn, Lys,
  N-epsilon,N- epsilon-dimethyllysine, N-epsilon
  - acetimidyllysine,N-epsilon-phenylimidyllysine, Gln or
  Asn"

( i x ) FEATURE:
 ( A ) NAME/KEY: Modified-site
 ( B ) LOCATION: 2
 ( D ) OTHER INFORMATION: /product="OTHER"
  / note= "Xaa = Asn, Gln, Arg, Lys, homoarginine, Orn,
  N-epsilon,N- epsilon-dimethyllysine or N-epsilon
  - methyllysine"

( i x ) FEATURE:
 ( A ) NAME/KEY: Modified-site
 ( B ) LOCATION: 3
 ( D ) OTHER INFORMATION: /product="OTHER"
  / note= "Xaa = Pro, MeGly, Gly, Asp or Glu"

( i x ) FEATURE:
 ( A ) NAME/KEY: Modified-site
 ( B ) LOCATION: 4
 ( D ) OTHER INFORMATION: /product="OTHER"
  / note= "Xaa = Asn, Gln, Gly or Ala"

( i x ) FEATURE:
 ( A ) NAME/KEY: Modified-site
 ( B ) LOCATION: 5
 ( D ) OTHER INFORMATION: /product="OTHER"
  / note= "Xaa = Asp or Glu"

( i x ) FEATURE:
 ( A ) NAME/KEY: Modified-site
 ( B ) LOCATION: 6..10
 ( D ) OTHER INFORMATION: /product="OTHER"
  / note= "Xaa at positions 6-10 may be present or absent"

( x i ) SEQUENCE DESCRIPTION: SEQ ID NO:37:

Xaa Xaa Xaa Xaa Xaa Xaa Xaa Xaa Xaa Xaa
1       5          1 0

( 2 ) INFORMATION FOR SEQ ID NO:38:

( i ) SEQUENCE CHARACTERISTICS:
  ( A ) LENGTH: 10 amino acids
  ( B ) TYPE: amino acid
  ( C ) STRANDEDNESS:
  ( D ) TOPOLOGY: linear ( i i ) MOLECULE TYPE: peptide ( i x ) FEATURE:
  ( A ) NAME/KEY: Modified-site
  ( B ) LOCATION: 1
  ( D ) OTHER INFORMATION: /product="OTHER"
   / note= "Xaa = Arg, homoarginine, Orn, Lys,
   N-epsilon,N- epsilon-dimethyllysine, N-epsilon
   - acetimidyllysine,N-epsilon-phenylimidyllysine, Gln or
   Asn"

( i x ) FEATURE:
  ( A ) NAME/KEY: Modified-site
  ( B ) LOCATION: 2
  ( D ) OTHER INFORMATION: /product="OTHER"
   / note= "Xaa = Asn, Gln, Arg, Lys, homoarginine, Orn,
   N-epsilon,N- epsilon-dimethyllysine or N-epsilon
   - methyllysine"

( i x ) FEATURE:
  ( A ) NAME/KEY: Modified-site
  ( B ) LOCATION: 3
  ( D ) OTHER INFORMATION: /product="OTHER"
   / note= "Xaa = Pro, MeGly, Gly, Asp or Glu"

```
        ( i x ) FEATURE:
                ( A ) NAME/KEY: Modified-site
                ( B ) LOCATION: 4
                ( D ) OTHER INFORMATION: /product="OTHER"
                        / note= "Xaa = Asn, Gln, Gly or Ala"

( i x ) FEATURE:
                ( A ) NAME/KEY: Modified-site
                ( B ) LOCATION: 5
                ( D ) OTHER INFORMATION: /product="OTHER"
                        / note= "Xaa = Asp or Glu"

( i x ) FEATURE:
                ( A ) NAME/KEY: Modified-site
                ( B ) LOCATION: 6
                ( D ) OTHER INFORMATION: /product="OTHER"
                        / note= "Xaa = Lys, Arg, Orn or homoarginine"

( i x ) FEATURE:
                ( A ) NAME/KEY: Modified-site
                ( B ) LOCATION: 7..10
                ( D ) OTHER INFORMATION: /product="OTHER"
                        / note= "Xaa at positions 7-10 may be present or absent"

( x i ) SEQUENCE DESCRIPTION: SEQ ID NO:38:

Xaa  Xaa  Xaa  Xaa  Xaa  Xaa  Xaa  Xaa  Xaa  Xaa
        1                  5                            1 0

( 2 ) INFORMATION FOR SEQ ID NO:39:

( i ) SEQUENCE CHARACTERISTICS:
                ( A ) LENGTH: 6 amino acids
                ( B ) TYPE: amino acid
                ( C ) STRANDEDNESS:
                ( D ) TOPOLOGY: linear ( i i ) MOLECULE TYPE: peptide ( i x ) FEATURE:
                ( A ) NAME/KEY: Modified-site
                ( B ) LOCATION: 3..6
                ( D ) OTHER INFORMATION: /product="OTHER"
                        / note= "Xaa at positions 3-6 may be present or absent"

( x i ) SEQUENCE DESCRIPTION: SEQ ID NO:39:

Arg  Xaa  Xaa  Xaa  Xaa  Xaa
        1                  5

( 2 ) INFORMATION FOR SEQ ID NO:40:

( i ) SEQUENCE CHARACTERISTICS:
                ( A ) LENGTH: 6 amino acids
                ( B ) TYPE: amino acid
                ( C ) STRANDEDNESS:
                ( D ) TOPOLOGY: linear ( i i ) MOLECULE TYPE: peptide ( i x ) FEATURE:
                ( A ) NAME/KEY: Modified-site
                ( B ) LOCATION: 3..6
                ( D ) OTHER INFORMATION: /product="OTHER"
                        / note= "Xaa at positions 3-6 may be present or absent"

( x i ) SEQUENCE DESCRIPTION: SEQ ID NO:40:

Arg  Lys  Xaa  Xaa  Xaa  Xaa
        1                  5

( 2 ) INFORMATION FOR SEQ ID NO:41:

( i ) SEQUENCE CHARACTERISTICS:
                ( A ) LENGTH: 6 amino acids
                ( B ) TYPE: amino acid
```

(C) STRANDEDNESS:
(D) TOPOLOGY: linear (ii) MOLECULE TYPE: peptide (ix) FEATURE:
　　(A) NAME/KEY: Modified-site
　　(B) LOCATION: 4..6
　　(D) OTHER INFORMATION: /product="OTHER"
　　　　/ note= "Xaa at positions 4-6 may be present or absent"

(xi) SEQUENCE DESCRIPTION: SEQ ID NO:41:

Arg Lys Pro Xaa Xaa Xaa
1               5

(2) INFORMATION FOR SEQ ID NO:42:

(i) SEQUENCE CHARACTERISTICS:
　　(A) LENGTH: 6 amino acids
　　(B) TYPE: amino acid
　　(C) STRANDEDNESS:
　　(D) TOPOLOGY: linear (ii) MOLECULE TYPE: peptide (ix) FEATURE:
　　(A) NAME/KEY: Modified-site
　　(B) LOCATION: 5..6
　　(D) OTHER INFORMATION: /product="OTHER"
　　　　/ note= "Xaa at positions 5-6 may be present or absent"

(xi) SEQUENCE DESCRIPTION: SEQ ID NO:42:

Arg Lys Pro Asn Xaa Xaa
1               5

(2) INFORMATION FOR SEQ ID NO:43:

(i) SEQUENCE CHARACTERISTICS:
　　(A) LENGTH: 6 amino acids
　　(B) TYPE: amino acid
　　(C) STRANDEDNESS:
　　(D) TOPOLOGY: linear (ii) MOLECULE TYPE: peptide (ix) FEATURE:
　　(A) NAME/KEY: Modified-site
　　(B) LOCATION: 6
　　(D) OTHER INFORMATION: /product="OTHER"
　　　　/ note= "Xaa at position 6 may be present or absent"

(xi) SEQUENCE DESCRIPTION: SEQ ID NO:43:

Arg Lys Pro Asn Asp Xaa
1               5

(2) INFORMATION FOR SEQ ID NO:44:

(i) SEQUENCE CHARACTERISTICS:
　　(A) LENGTH: 6 amino acids
　　(B) TYPE: amino acid
　　(C) STRANDEDNESS:
　　(D) TOPOLOGY: linear (ii) MOLECULE TYPE: peptide (xi) SEQUENCE DESCRIPTION: SEQ ID NO:44:

Arg Lys Pro Asn Asp Lys
1               5

THROMBIN RECEPTOR ANTAGONISTS

CROSS REFERENCE TO RELATED APPLICATION

This is a Continuation of application Ser. No. 08/080,788, filed Jun. 28, 1993 (abandoned), which is a Continuation-In-Part of application Ser. No. 07/922,340, filed Jul. 30, 1992 (abandoned).

BACKGROUND OF THE INVENTION

This invention relates to materials which modulate the action of thrombin on cells of the vascular and circulating blood system. It is well known that thrombin has multiple activities. Perhaps the most well known activity of this serine protease is to convert fibrinogen to fibrin which clots blood. Additional functions of thrombin are widespread and diverse and appear to involve cellular activations which are mediated through cellular thrombin receptor(s). For example, thrombin is the most potent activator of platelets; it is chemotactic for monocytes; it is mitogenic for lymphocytes and mesenchymal cells including vascular smooth muscle cells and; it promotes numerous responses within the vascular endothelium. See, Coughlin, et al., *J. Clin. Invest.* 89:351–355 (1992). Because these cell activating functions of thrombin occur within the range of concentrations normally required for the clotting of blood, thrombin has been proposed to play important physiological roles not only in hemostasis and thrombosis but may also have principle roles in mediating responses to vascular injury such as leukocyte chemotaxis to mediate inflammation, cellular proliferation to mediate restenosis, glomerulonephritis, and wound repair such as occurs in bone remodeling.

The role of thrombin in acute thrombosis has been clearly established. For a review, see, Chesbro et al., *Thromb. Haemostas.*, 66:1–5 (1991). However, thrombin's role in thrombosis is not limited to its blood clotting activity but also extends to platelet aggregation as thrombin appears to be the principle physiological mediator of platelet aggregate formation at sites of vascular injury resulting from the activation of the platelet thrombin receptor. Recent antithrombotic approaches inhibit or modulate the enzymatic activity of thrombin and include compounds such as heparin, low molecular weight heparins, PPACK, hirudins, argatroban, and the hirulogs. All of these agents inhibit the catalytic activity of the enzyme. Therefore, these agents not only inhibit the pro- and anticoagulant actions of thrombin but also the cell activating functions of thrombin as well. Accordingly, none of these agents are useful for specifically inhibiting the cellular actions of thrombin. No agent which specifically targets the thrombin receptor has been clinically developed. Previous attempts to identify a thrombin receptor inhibitor have been thwarted by the inability of researchers, until very recently, to identify the physiologically relevant and functional thrombin receptor.

Thrombin has numerous effects on a variety of cells outside of platelets. For example, thrombin is mitogenic for smooth muscle and endothelial cells. Thrombin is also known to increase vascular permeability and to induce vasoconstriction. See, Malik, *Semin. Thromb. Hemostasis.* 12:184–196 (1986). Thrombin can also induce the production and release of several constituents from endothelial cells including platelet-derived growth factor (PDGF), prostacyclin, platelet-activating factor (PAF), tissue plasminogen activator and plasminogen activator inhibitor. Finally, thrombin is capable of promoting the adherence of platelets, neutrophils, monocytes and T cells. For review, see, Shuman, *Ann. NY Acad. Sci.* 485:228–239, (1986). All of these actions of thrombin are likely to be mediated by cellular thrombin receptors identical or nearly identical to the cloned thrombin receptor and suggest that thrombin may also play a central role in initiating inflammatory and cellular proliferative responses to vascular injury linking it with the coagulation and hemostasis cascades. While most of these responses to thrombin suggest such a linkage between hemostasis and vascular repair, this hypothesis remains to be tested. Agents which specifically effect the activation of thrombin receptor(s) within cells are ideally suited to this purpose.

Restenosis, the vascular hyperproliferative response to blood vessel wall injury induced by interventional procedures such as coronary angioplasty, may be stimulated by thrombin-induced cellular events as sites of injury either directly or indirectly. Cellular proliferation may be simulated indirectly by the release of potent growth factors from locally adherent platelets or by the action of thrombin on endothelial cells which could release PDGF upon stimulation. Smooth muscle cell proliferation within diseased vessels may also be stimulated directly by thrombin due to the high local concentration of thrombin generated at the vascular injury sites created by the active platelet-rich thrombus. Indeed, recent studies with the potent thrombin inhibitor hirudin suggest that thrombin plays such a role in the restenosis process, but it is not known for these studies whether thrombin's effect is direct or indirect. See, Sarembock, et al., *Circulation*, 84:232–243, (1992).

Although the cellular actions of thrombin have the potential for causing various pathological conditions, there are no known therapeutic agents which specifically block the cellular actions of thrombin. Recently, however, a functional thrombin receptor cDNA has been cloned and expressed from megakaryoblastic cells lines, and the presence of mRNA encoding this receptor has been demonstrated in human platelets and vascular endothelial cells. See, Vu, et al., *Cell*, 64:1057–1068 (1991). This development has created significant opportunities to develop highly specific agents which target the cellular thrombin receptor.

Close inspection of the predicted amino acid sequence of the thrombin receptor revealed a potential recognition and thrombin cleavage sequence within the 100-residue amino terminal domain of the receptor. Subsequent mutagenesis studies of the receptor has demonstrated that this cleavage site is required for thrombin-mediated receptor signaling through proteolytic cleavage at this site. See, Vu, et al., *Nature*, 353:674–677 (1991). These experiments confirmed previous suggestions that proteolysis of a putative thrombin receptor might be responsible for thrombin receptor activation but left unanswered how proteolysis mediates receptor signaling.

Two potential explanations for thrombin-induced signaling have been postulated. The first is that proteolytic removal of the 15-residue segment at the amino terminus of the receptor induces a conformational change in the receptor leading to receptor activation. Alternatively a specific "tethered ligand" sequence unmasked upon receptor proteolysis may directly interact with a "ligand binding site" within the body of the receptor leading to receptor activation. While both of these potential mechanisms are quite similar, if not semantic, it appears that the "tethered ligand" hypothesis is the more likely explanation for receptor signaling. Synthetic peptides which mimic the new amino acid sequence revealed upon receptor proteolysis function as full agonists of the platelet receptor even in the absence of proteolytic cleavage of the receptor. This suggests that the new amino acid sequence at the amino terminus of the receptor revealed upon cleavage of the receptor functions as a "tethered ligand" and interacts at a distal "binding site". These effects have been confirmed with the hamster receptor activated with the hamster "tethered ligand" peptide. See, Vouret-Craviari, et al., *Mol. Biol. Cell.* 3:95–102, (1992). Additional studies with agonist peptides have confirmed the similarity of putative thrombin receptors present in platelets, endothelial cells, fibroblasts and smooth muscle cells. See, Hung et al., *J. Cell. Biol.* 116:827–832, (1992) and Ngaiza and Jaffe, *Biochem. Biophys. Res. Commun.* 179:1656–1661 (1991).

Most research conducted to date on modulating the actions of thrombin have been directed toward non-specific inhibition of the catalytic activity of thrombin. These efforts have resulted in thrombin inhibitors which effect both the pro- and anti-coagulant actions of thrombin. For a review, see, Chesbro and Fuster, *Circulation*, 83:1815–1817 (1991). Certain investigators have also attempted to inhibit the cellular activities of thrombin by using polypeptides prepared from the sequence of thrombin. See, Carney and Glenn, International Patent Application Under the PCT, No. WO 88/03151, 5 May 1988. Another report has focused on the preparation of certain dipeptides and analogs which appear to inhibit thrombin-cellular activities without effecting the catalytic activity of thrombin. See, Ruda, et al., *Biochem. Pharmacol.* 39:373–381 (1990). Both of these approaches display a certain degree of specificity but are limited due to their lack of potent effects.

Structure-activity studies using the thrombin receptor agonist peptide sequences have also been reported. A pentapeptide sequence, Phe-Leu-Leu-Arg-Asn-OH, based on a portion of the agonist peptide minimum structure has been shown to be a weak antagonist of platelet thrombin receptors activated with either thrombin or thrombin receptor agonist peptides. See, Vassallo, et al., *J. Biol. Chem.* 267:6081–6085 (1992).

A different approach to receptor antagonism has been investigated by others who have raised antibodies against a peptide sequence within the amino-terminal domain of the thrombin receptor which appears to be a binding/recognition site for thrombin. Thee antibodies effectively and specifically block thrombin-induced responses in platelets, thereby acting as antagonists of the thrombin receptor. See, Hung et al., *J. Clin. Invest.* 89:1350–1353 (1992).

The lack of potency and/or specificity of the above described approaches to thrombin receptor antagonism limits their utility as thrombin receptor antagonists. Thus, highly potent and specific inhibitors of the thrombin receptor are the focus of this invention.

SUMMARY OF THE INVENTION

Peptide derivatives which act as potent and highly specific thrombin receptor antagonists have now been discovered. These antagonists exhibit specificity for the cellular thrombin receptor, which allows them to modulate cellular responses such as platelet aggregation without interfering with certain desired catalytic activities of thrombin, such as the conversion of fibrinogen to fibrin. These peptide derivatives include peptides and modified peptides which contain functional groups that enhance in vivo stability and therapeutic potential.

The peptide derivatives of the present invention bind to cellular thrombin receptors and inhibit the activation of the receptor induced by thrombin. Included among the thrombin receptor antagonists of the invention are small peptide derivatives and peptide analogs containing isosteric replacements for labile amide linkages. This preferred class of peptide derivatives offers an even greater improvement in therapeutic potential since the structure of peptide derivatives of this type renders them less susceptible to proteolytic inactivation.

The invention also resides in pharmaceutical compositions containing the peptide derivatives described above. These compositions are useful as anti-thrombotics and are also useful in clinical applications including treatment of abrupt closure during angioplasty, treatment of restenosis in the context of angioplasty, and the treatment of unstable angina, myocardial infarction and certain forms of thrombotic or thromboembolytic stroke. The peptide derivatives of the invention may be used alone or in combination with other therapeutic agents such as urokinase and tPA. These compositions are also useful as anti-inflammatory, anti-restenosis agents and may be used to treat and/or prevent glomerulonephrotic syndromes.

DETAILED DESCRIPTION OF THE INVENTION

As used herein, the term "alkyl" refers to a saturated hydrocarbon radical which may be straight-chain or branched-chain (for example, ethyl, isopropyl, t-amyl, or 2,5-dimethylhexyl). This definition applies both when the term is used alone and when it is used as part of a compound term, such as "aralkyl" and similar terms. Preferred alkyl groups are those containing 1 to 10 carbon atoms. All numerical ranges in this specification and claims are intended to be inclusive of their upper and lower limits.

The term "cycloalkyl" refers to a saturated hydrocarbon ring. Preferred cycloalkyl moities are those having 3 to 8 carbon atoms in the ring. Additionally, the term "(cycloalkyl)alkyl" refers to a group having a cycloalkyl moiety attached to an alkyl moiety. Examples are cyclohexylmethyl, cyclohexylethyl and cyclopentylpropyl.

The term "alkenyl" as used herein refers to an alkyl group as described above which contains one or more sites of unsaturation.

The term "alkoxy" refers to an alkyl radical as described above which also bears an oxygen substituent which is capable of covalent attachment to another hydrocarbon radical (such as, for example, methoxy, ethoxy, phenoxy and t-butoxy).

The term "aryl" refers to an aromatic substituent which may be a single ring or multiple rings which are fused together, linked covalently or linked to a common group such as an ethylene or methylene moiety. The aromatic rings may each contain heteroatoms, for example, phenyl, naphthyl, biphenyl, diphenylmethyl, 2,2-diphenyl-1-ethyl, thienyl, pyridyl and quinoxalyl. The aryl moieties may also be optionally substituted with halogen atoms, or other groups such as nitro, carboxyl, alkoxy, phenoxy and the like. Additionally, the aryl radicals may be attached to other moieties at any position on the aryl radical which would otherwise be occupied by a hydrogen atom (such as, for example, 2-pyridyl, 3-pyridyl and 4-pyridyl).

The terms "arylalkyl", "arylalkenyl" and "aryloxyalkyl" refer to an aryl radical attached directly to an alkyl group, an alkenyl group, or an oxygen which is attached to an alkyl group, respectively.

The term "basic moiety" refers to a group which is capable of accepting a proton, or donating a pair of electrons in hydrogen bonding. Examples of basic moieties are amines, guanidines, imidates, and nitrogen-containing heterocycles such as pyridine, imidazole, triazole and pyrimidine.

The term "hydrocarbon radical" refers to alkyl, alkenyl, alkoxy or aryl radical or any combination thereof.

The term "hydrophobic radical" refers to a group which lowers the water solubility of a molecule. Preferred hydrophobic radicals are groups containing at least 3 carbon atoms.

The terms "isostere" and "isosteric replacement" are used interchangeably to refer to groups which have similar electronic or spatial properties. In the context of the present invention, for example, —CONH— may be replaced by —CH$_2$NH—, —NHCO—, —SO$_2$NH—, —CH$_2$O—, —CH$_2$CH$_2$—, —CH$_2$S—, —CH$_2$SO—, —CH=CH— (cis or trans), —COCH$_2$—, —CH(OH)CH$_2$— and 1,5-disubstituted tetraole such that the radicals linked by these isosteres would be held in similar orientations to radicals linked by CONH. For a general review of these and other isosteres see, Spatola, A. F., in *Chemistry and Biochemistry of Amino Acids, Peptides and Proteins*, B. Weinstein, eds., Marcel Dekker, New York, p. 267 (1983).

The term "neutral amino acid side chain" refers to that portion of an amino acid which is attached to the carbon adjacent to the carbonyl and which has no formal charge at physiological pH. Examples of neutral amino acid side chains are hydroxymethyl (from serine) and mercaptomethyl (from cysteine).

For the compounds of the invention which contain amino acid or peptide fragments, the amino acid residues are denoted by single-letter or three-letter designations following conventional practices. The designations for gene-encoded amino acids are as follows:

| Amino Acid | One-Letter Symbol | Three-Letter Symbol |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

Commonly encountered amino acids which are not gene-encoded may also be used in the present invention. These amino acids and their abbreviations include ornithine (Orn); t-butylglycine (t-BuG); phenylglycine (PhG); cyclohexylalanine (Cha); norleucine (Nle); 2-naphthylalanine (2-Nal); 1-naphthylalanine (1-Nal); 2-thienylaniline (2-Thi); 1,2,3,4-tetrahydroisoquinoline-3-carboxylic acid (Tic); N-methylisoleucine (N-MeIle), homoarginine (Har), Nα-methylarginine (N-MeArg) and sarcosine (Sar).

All of the amino acids used in the present invention may be either the D- or L-isomer. The L-isomers are preferred.

The compounds of the present invention bind to the thrombin receptor but will not activate it. These antagonists are represented by the formula:

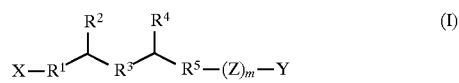

The groups R$^1$ and R$^3$ in this formula are the same or different, each being either an amide linkage, an N-alkylamide linkage, or an isosteric replacement of these linkages.

The groups R$^2$ and R$^4$ are likewise the same or different, and each is a hydrophobic radical. Examples of hydrophobic radicals for these groups are phenyl, t-butyl, isopropyl, isobutyl, cyclohexylmethyl, 1-adamantylmethyl, cyclopentylmethyl, cycloheptylmethyl, benzyl, 4-hydroxybenzyl, 2-naphthylmethyl, 1-naphthylmethyl, 2-thienylmethyl, methylthioethyl, indolylmethyl, and substituted benzyl. In preferred structures, either R$^2$ or R$^4$ is cyclohexylmethyl, or both are cyclohexylmethyl. In addition, R$_2$ is any amino acid side chain which does not carry a formal charge at physiological pH. Examples of neutral amino acid side chains are hydroxymethyl and mercaptomethyl.

The group R$^5$ is either CO, CH$_2$ or SO.

The symbol X represents a variety of structures. Some of these structures are represented by the formula:

in which R$^6$ and R$^7$ are the same or different, each being either H, alkyl, (cycloalkyl)alkyl, alkoxyalkyl, alkylthioalkyl or arylalkyl; and R$^8$ is a hydrophobic radical. Preferred groups for R$^6$ and R$^7$ are H, C$_1$–C$_{10}$ alkyl, (C$_1$–C$_8$ cycloalkyl)-(C$_1$–C$_4$ alkyl), (C$_1$–C$_{10}$ alkoxy)-(C$_1$–C$_{10}$ alkyl), (C$_1$–C$_{10}$ alkylthio)-(C$_1$–C$_{10}$ alkyl), aryl-(C$_1$–C$_6$ alkyl), with the proviso that at least one of R$^6$ and R$^7$ is other than H. Preferred groups for R$^8$ are those which are at least as hydrophobic as an isopropyl group. Particularly preferred are benzyl and phenethyl. Other structures for X are hydrophobic residues which contain aryl moieties. Preferred among these are arylalkyl, arylalkenyl, aryloxyalkyl, biphenyl, 1,2,3,4-tetrahydronaphthyl, indolylmethyl, quinolinyl, isoquinolinyl, 1,2,3,4-tetrahydroisoquinolinyl, 1,2,3,4-tetrahydroquinolinyl, N-alkyl and N-(cycloalkyl)alkyl 1,2,3,4-tetrahydroisoquinolinyl, and N-alkyl 1,2,3,4-tetrahydroquinolinyl. Specific examples of X groups which are hydrophobic residues containing aryl moieties are 1-phenyloct-1-en-2-yl, 1-phenoxy-1-propyl, 1-(2-naphthyloxy)-1-heptyl, 1-phenoxy-1-pentyl, 1-(1-naphthyloxy)-1-pentyl, biphenyl, 1-naphthyl, 2-naphthyl, 1,2,3,4-tetrahydronaphth-2-yl, indolylmethyl, 2-quinolyl, 3-quinolinyl, N-pentyl- 1,2,3,4-tetrahydroisoquinolinyl, and N-cyclohexylmethyl-1,2,3,4-tetrahydroisoquinolinyl.

Of the remaining groups, Y is an alkoxy, hydroxy, amino, alkylamino, dialkylamino, or a substituted alkoxy or alkylamino group. Preferred groups for Y are those having the formulas OR$^9$ or NR$^{10}$R$^{11}$ wherein R$^9$, R$^{10}$ and R$^{11}$ are the same or different, each being either H, C$_1$–C$_{10}$ alkyl, or a hydrocarbon radical substituted with a basic moiety. Further preferred among these are NR$^{10}$R$^{11}$ where R$^{10}$ and R$^{11}$ are H or C$_1$–C$_4$ alkyl. The letter m denotes an integer which is zero or one, and the group Z, when present, is an amino acid or peptide residue, preferred peptide residues being those containing 2 to 20 amino acids.

In certain preferred embodiments, X is of Formula II where R$^6$ is H and R$^7$ is C$_1$–C$_{10}$ alkyl, (C$_1$–C$_8$ cycloalkyl)

-($C_1$–$C_4$ alkyl), ($C_1$–$C_{10}$ alkylthio)-($C_1$–$C_{10}$ alkyl), or aryl-($C_1$–$C_6$ alkyl). In further preferred embodiments, $R^6$ and $R^7$ are both $C_1$–$C_{10}$ alkyl.

In further preferred embodiments, X is of Formula II where $R^6$ is H, $R^7$ is alkyl and $R^8$ is arylalkyl. In further preferred embodiments, $R^1$ and $R^3$ are both CONH, $R^2$ and $R^4$ are hydrophobic radicals of at least three carbons each, $R^5$ is CO, Z is a peptide of between two and ten amino acids, and Y is an amine.

In still further preferred embodiments, X has the formula above wherein $R^6$ is H, $R^7$ is pentyl and $R^8$ is benzyl. Additionally, $R^1$ and $R^3$ are both CONH, $R^2$ and $R^4$ are alkyl or cycloalkylalkyl of at least three carbons each, $R^5$ is CO, and Z is a peptide of the formula $(AA^i)_n$ in which AA is an amino acid and i is an integer denoting its position downstream from $R^5$. An $AA^i$ at any position may be the same or different from an $AA^i$ at any other position. $AA^1$ is preferably Arg, Har, Orn, Lys, Nε,Nε-Dimethyl-Lys, Nε-Acetimidyl-Lys, Nε-Phenylimidyl-Lys, Gln or Asn; $AA^2$ is preferably Asn, Gln, Arg, Lys, Har, Orn, Nε,N68-Dimethyl-Lys or Nε-Methyl-Lys; $AA^3$ when present is Pro, Sar, Gly, Asp or Glu, with n being 3 to 10 and preferably 3 to 6; $AA^4$, when n is 4 to 10 or 4 to 6, is preferably Asn, Gln, Gly or Ala; $AA^5$, when n is 5 to 10 or 5 to 6, is Asp or Glu; and $AA^6$, when n is 6 to 10, is preferably Lys, Arg, Orn and Har; and Y is $NH_2$ (SEQ ID NO:1).

The most preferred embodiments are those in which X is represented by Formula II, wherein $R^6$ is H, $R^7$ is pentyl and $R^8$ is benzyl. Additionally, $R^1$ and $R^3$ are both CONH, $R^2$ and $R^4$ are both cyclohexylmethyl, $R^5$ is CO, Z is a peptide of the formula $(AA^i)_n$ where n is between 2 and 6 and $AA^1$ is Arg and $AA^2$ is Lys, Arg or Har, and Y is $NH_2$ (SEQ ID NO:2).

In another group of preferred embodiments, X is a hydrophobic radical containing at least one aromatic ring. Additionally, $R^1$ and $R^3$ are independently either CONH or $CH_2NH$, $R^2$ and $R^4$ are hydrophobic radicals of at least four carbons each, $R^5$ is CO, Z is a peptide of between two and six amino acids and Y is an amine (SEQ ID NO:3).

Further preferred embodiments within this group are those in which X is aryloxyalkyl, $R^1$ and $R^3$ are independently either CONH or $CH_2NH$, $R^2$ and $R^4$ are independently either isobutyl, benzyl or cyclohexylmethyl, $R^5$ is CO, Z is a peptide of between two and six amino acids and Y is an amine (SEQ ID NO:3).

In the most preferred embodiments of this group, X is aryloxyalkyl, $R^1$ and $R^3$ are independently either CONH or $CH_2NH$, $R^2$ and $R^4$ are independently either isobutyl, benzyl or cyclohexylmethyl, $R^5$ is CO, Z is a peptide of the formula $(AA^i)_n$ where n is between 2 and 6 and $AA^1$ is Arg and $AA^2$ is Lys, Arg or Har, and Y is $NH_2$ (SEQ ID NO:2).

The compounds of the present invention further include those compounds in which any or all amide groups (CONH) which would otherwise be present have been alkylated (for example, CON(Me)) or replaced by suitable isosteres. Examples of isosteres of CONH are —$CH_2NH$—, —$CH_2CH_2$—, —$CH_2S$—, —$CH_2SO$—, —$COCH_2$—, —CH(OH)$CH_2$— and —CH=CH—, —NHCO—, —$SO_2NH$—, —$CH_2O$— and 1,5-disubstituted tetrazole.

The compounds of the present invention which terminate with a carboxylic acid further include any pharmaceutically acceptable salts or esters of the acid.

The thrombin receptor antagonists of the present invention may be prepared by solid phase peptide synthesis which is extensively described and used in the art to prepare peptides. The compounds may also be prepared using liquid phase synthetic methods which are also well known in the art. See, M. Bodanszky and A. Bodanszky, *The Practice of Peptide Synthesis* (1984) and M. Bodanszky, *Principles of Peptide Synthesis* (1984).

Synthesis of peptide analogs containing isosteric replacements, following chemical procedures which are known to those of skill in the art, are outlined below.

Additional aspects of the invention are directed to pharmaceutical compositions containing the compounds of the invention. These compounds are usefull for example, in the treatment of myocardial infarction, unstable angina, abrupt closure, restenosis following angioplasty, inflammation and wound healing. The antagonists of the invention may be administered in conventional formulations. One common formulation might include a saline solution buffered to pH 7.4, and suitable for administration by injection. Formulations for bolus administration are also useful, and comprise the selected antagonist with pharmaceutically acceptable excipients such as starch or gum arabic as binding agents. Other typical formulations may be found in *Remington's Pharmaceutical Sciences*, Mack Publishing Co., Easton, Pa., latest edition.

Systemic administration of the compounds is typically carried out by injection, preferably by intravenous injection. Alternatively, intramuscular, intraperitoneal or subcutaneous injection may be used. Other forms of systemic administration of the compounds such as transdermal or transmucosal administration are also possible. Oral administration may also be used with properly formulated enteric or encapsulated formulations.

The dosage used will depend on such factors as the choice of antagonist, the route of administration, the nature of the formulation, the nature of the patient's illness and the judgment of the attending physician. Typically, the dosage will be in the range of 0.1–100 μg/kg of subject. More preferably, the dosage will be in the range of 1–50 μg/kg of subject.

The following experimental results are offered by way of example and not by way of limitation.

EXAMPLE 1

Synthesis of (N,N-di-n-pentyl-Phe)-Cha-Cha-Arg-Lys-$NH_2$ (SEQ ID NO:4)

Starting with 0.5 mmol of p-methylbenzhydrylamine•HCl resin (from Applied Biosystems), the resin was neutralized with diisopropylethyl amine and coupled with Nα-t-BOC-Nε-(2-chloro-CBZ)-L-lysine using N,N-dicyclohexylcarbodiimide (DCC) and 1-hydroxybenzotriazole (HOBt) in N-methylpyrrolidinone (NMP) as solvent followed by deprotection with trifluoroacetic acid (TFA) in dichloromethane. Successive couplings and deprotections were performed with Boc-Arg(Tos), Boc-Cha, Boc-Cha and Boc-Phe. Following removal of the Boc group from the Phe residue with the aid of TFA, the resin was washed to afford the peptide resin trifluoroacetate. To this resin, which was suspended in DMF, 2.5 equivalents of n-valeraldehyde in dimethylformamide (DMF) (containing 1% acetic acid) was added followed by treatment with 2.5 equivalents of $NaBH_3CN$ for 60 min at room temperature. Aliquots of resin were removed periodically to check for completeness of alkylation by ninhydrin reaction. When the alkylation was determined to be complete, the resin was washed with DMF, $CH_2Cl_2$, and methanol and dried in vacuo. The peptide was cleaved from the resin and the protecting groups were removed by treatment with anhydrous HF containing 10% anisole and 2% methyl ethyl sulfide. The resin/peptide mixture was extracted with 25% acetic acid solution and lyophilized to afford the crude peptide as a white powder. Subsequent purification of the peptide on a $C_{18}$ reversed phase column employing a gradient elution (10–60% $CH_3CN$ in water containing 0.1% TFA) provided the desired peptide. FAB mass spectrum, calcd. mass 895, observed M+1 896.

EXAMPLE 2

Synthesis of 2-Phenoxybutyryl-Cha-Cha-Arg-Lys-$NH_2$ (SEQ ID NO:5)

Synthesis of the peptide resin up to Cha-Cha-Arg-Lys-MBHA resin (SEQ ID NO:6) was performed as described in Example 1. Acylation of the peptide resin with (±)2-phenoxybutyric acid was carried out using DCC in NMP with HOBt. The resulting resin was washed and the peptide was cleaved, deprotected and purified using the conditions in Example 1. FAB mass spectrum, calcd. mass 770, observed M+1 771.

EXAMPLE 3

Synthesis of (N-n-pentyl-Tic)-Cha-Cha-Arg-Lys-$NH_2$ (SEQ ID NO:7)

Synthesis of the peptide resin to Tic-Cha-Cha-Arg-Lys-MBHA resin (SEQ ID NO:8) was performed as in Example 1, substituting Boc-Tic for Boc-Phe. After removal of the Boc group from the Tic residue, the resin was reductively alkylated with n-valeraldehyde under the conditions of Example 1. The resin was washed and the peptide was cleaved, deprotected and purified using the conditions above. FAB mass spectrum, calcd. mass 837, observed M+1 838.

EXAMPLE 4

Synthesis of Phenyl—CH=C(($CH_2$)$_5$—$CH_3$)—$CH_2$-Cha-Cha-Arg-Lys-$NH_2$ (SEQ ID NO:9)

Synthesis of the peptide resin up to TFA·$NH_2$-Cha-Cha-Arg-Lys-MBHA (SEQ ID NO:10) was performed as described in Example 1. The amino group was reductively alkylated using 2.5 equivalents of phenyl—CH=C(($CH_2$)$_5$—$CH_3$)—CHO in DMF with $NaBH_3CN$ for 2 h at room temperature. The resin was washed and dried and the peptide was cleaved, deprotected and purified using the above conditions. FAB mass spectrum, calcd. mass 803, observed M+1 804.

EXAMPLE 5

Assay for Thrombin Receptor Antagonist Activity

The compounds of the present invention may be tested for thrombin receptor antagonist activity by using a platelet aggregation assay. In this assay, washed human platelets are prepared from blood drawn from healthy volunteers who have not ingested any medications for two weeks prior to donation. Blood is drawn into 12.5% (vol/vol) ACD (85 mM sodium citrate, 111 mM dextrose, 71 mM citric acid) containing 0.1% (vol/vol) $PGI_2$ (0.05 mg/mL $PGI_2$, 100 mM Tris, pH 12). Platelet-rich plasma was obtained by centrifugation at 160×g for 20 minutes. The platelets were pelleted by centrifugation at 760×g for 10 minutes and resuspended in CGS (13 mM trisodium citrate, 120 mM sodium chloride, 30 mM dextrose, pH 7.0) containing 0.1% (vol/vol) $PGI_2$, repelleted and resuspended in Tyrodes buffer (10 mM Hepes, 12 mM sodium bicarbonate, 138 mM sodium chloride, 5.5 mM glucose, 2.9 mM potassium chloride, 1.0 mM calcium chloride, pH 7.4) and stored at 37° C. Approximately 0.4–10 nM α-thrombin is used to stimulate platelet aggregation in control reactions which are monitored by aggregometry using an aggregometer. Candidate antagonists are added to the platelet mixture followed by the addition of thrombin in order to assess their ability to prevent thrombin-mediated aggregation.

Platelet aggregation can also be measured with washed platelets in 96-well microtiter plates as described in Fratantoni, J. C. et al., *Am. J. Clin. Pathol.* 94:613–617 (1990). The ability of the antagonists to block the thrombin receptor was assessed in this assay using various concentrations of antagonists. The concentration at which 50% inhibition of platelet aggregation is achieved is defined as $IC_{50}$.

The following table lists $IC_{50}$ values for representative compounds of the invention.

TEST RESULTS

| SEQ ID NO: | Compound No. | Structure | $IC_{50}$ (μM) |
|---|---|---|---|
| 11 | 1 | 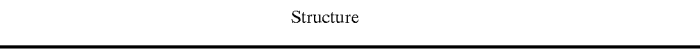 | 5 |

-continued

TEST RESULTS

| SEQ ID NO: | Compound No. | Structure | IC$_{50}$ ($\mu$M) |
|---|---|---|---|
| 11 | 2 | (Phe)(Cha)(Cha) with N-(3-methylthiopropyl) group — RKPNDK—NH$_2$ | 10 |
| 11 | 3 | (Phe)(Cha)(Cha) with N-heptyl group — RKPNDK—NH$_2$ | 10 |
| 11 | 4 | (Phe)(Cha)(Cha) with N-butyl group — RKPNDK—NH$_2$ | 5 |
| 11 | 5 | (Phe)(Cha)(Cha) with N-pentyl group — RKPNDK—NH$_2$ | 2.5 |
| 11 | 6 | (Phe)(Cha)(Cha) with N-(2-cyclopentylethyl) group — RKPNDK—NH$_2$ | 10 |
| 11 | 7 | (Phe)(Cha)(Cha) with N-(3-phenylpropyl) group — RKPNDK—NH$_2$ | 5 |

-continued

TEST RESULTS

| SEQ ID NO: | Compound No. | Structure | IC$_{50}$ ($\mu$M) |
|---|---|---|---|
| 11 | 8 | 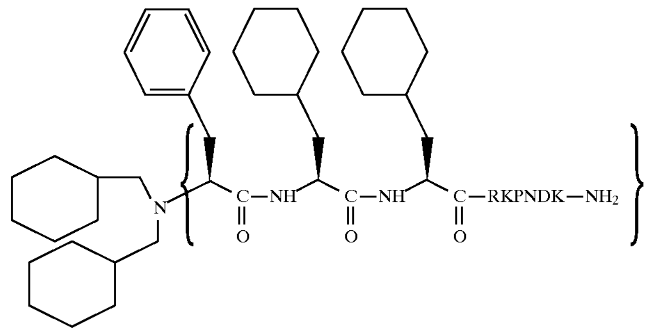 | 5 |
| 12 | 9 | 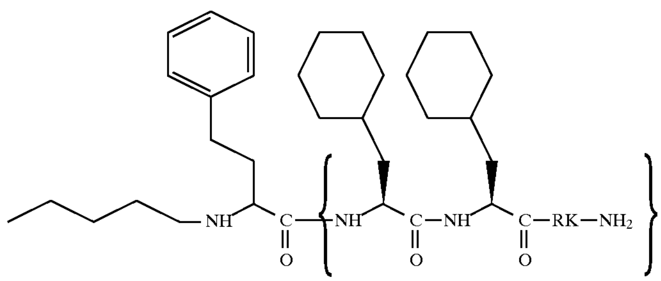 | 15 |
| 5 | 10 | 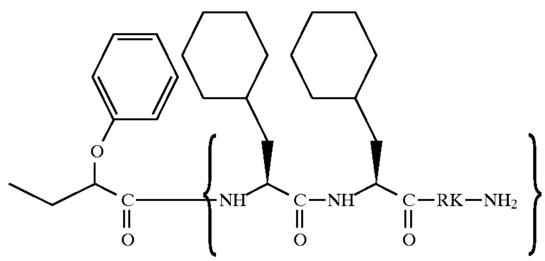 | 10 |
| 7 | 11 | 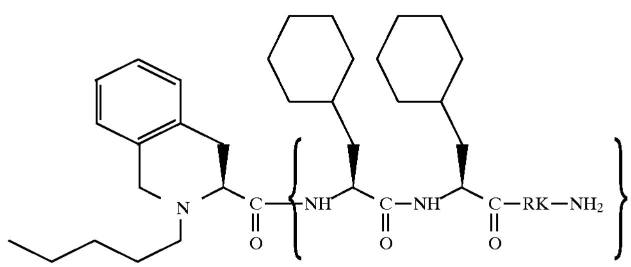 | 2.5 |
| 13 | 12 | 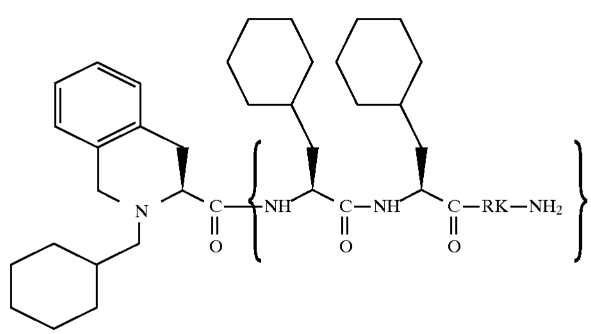 | 20 |

-continued
TEST RESULTS
| SEQ ID NO: | Compound No. | Structure | IC$_{50}$ ($\mu$M) |
|---|---|---|---|
| 14 | 13 | 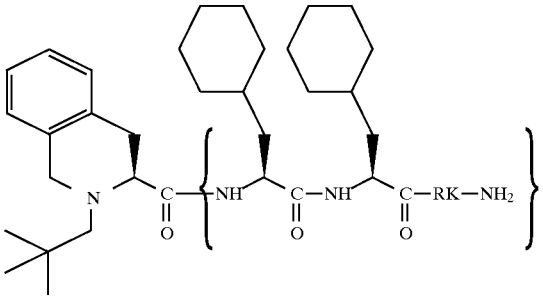 | 5 |
| 15 | 14 | 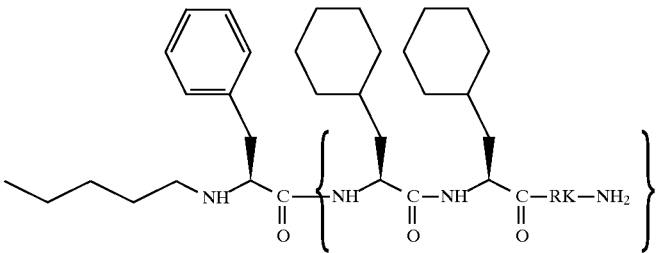 | 5 |
| 16 | 15 | 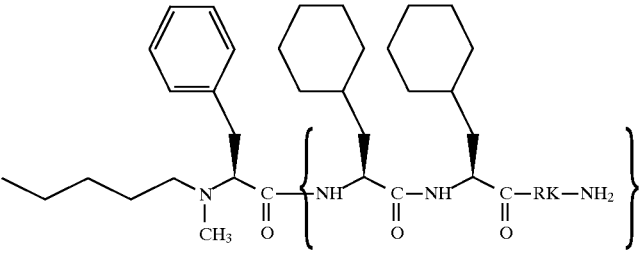 | 10 |
| 17 | 16 | 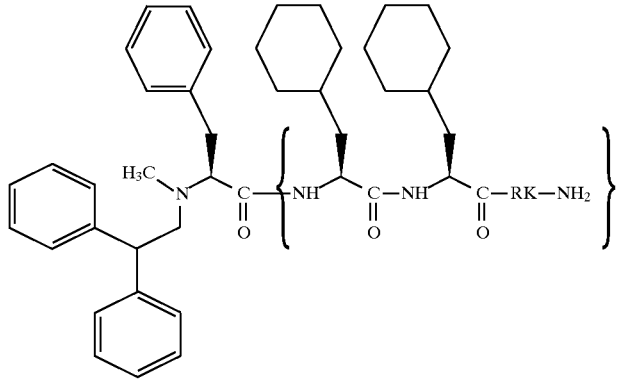 | 10 |
| 17 | 17 | 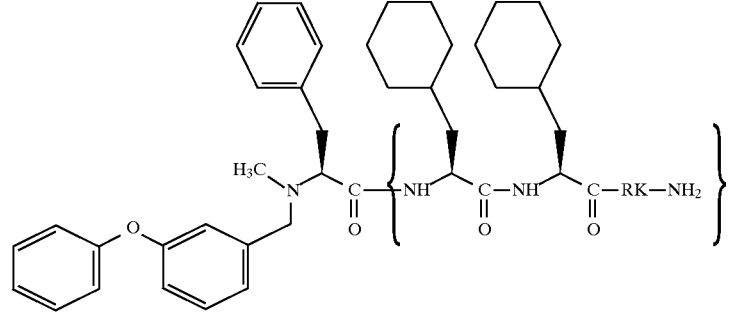 | 15 |

-continued

TEST RESULTS

| SEQ ID NO: | Compound No. | Structure | IC$_{50}$ ($\mu$M) |
|---|---|---|---|
| 17 | 18 | | 5 |
| 17 | 19 | | 30 |
| 17 | 20 | | 15 |
| 4 | 21 | 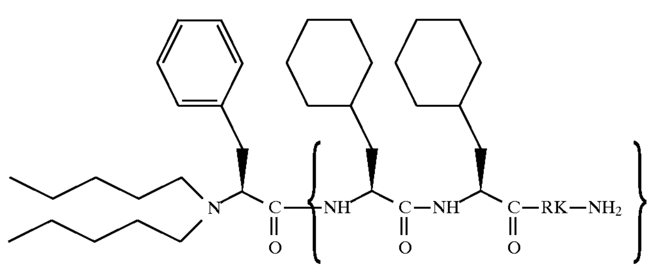 | 10 |
| — | 22 | 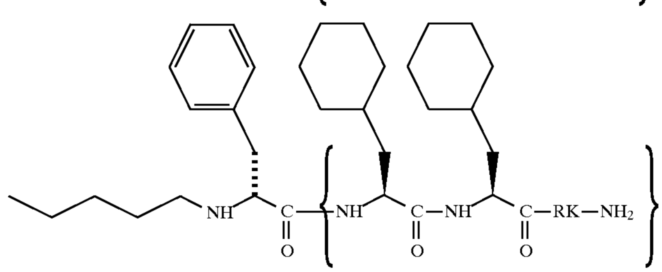 | 25 |

-continued

TEST RESULTS

| SEQ ID NO: | Compound No. | Structure | IC$_{50}$ ($\mu$M) |
|---|---|---|---|
| 18 | 23 | (2-naphthyloxy)-substituted heptanoyl-{NH-CH(Cy)-CO-NH-CH(Cy)-CO-RK-NH$_2$} | 5 |
| 18 | 24 | (phenoxy)-substituted pentanoyl-{NH-CH(Cy)-CO-NH-CH(Cy)-CO-RK-NH$_2$} | 15 |
| 18 | 25 | biphenyl-2-carbonyl-{NH-CH(Cy)-CO-NH-CH(Cy)-CO-RK-NH$_2$} | 25 |
| 18 | 26 | (2-benzylidene)octyl-{NH-CH(Cy)-CO-NH-CH(Cy)-CO-RK-NH$_2$} | 7.5 |
| 18 | 27 | (1-naphthyloxy)-substituted pentanoyl-{NH-CH(Cy)-CO-NH-CH(Cy)-CO-RK-NH$_2$} | 5 |
| 18 | 28 | quinoline-2-carbonyl-{NH-CH(Cy)-CO-NH-CH(Cy)-CO-RK-NH$_2$} | 30 |

-continued

TEST RESULTS

| SEQ ID NO: | Compound No. | Structure | IC$_{50}$ ($\mu$M) |
|---|---|---|---|
| 18 | 29 | quinoline-3-C(=O)-{NH-CH(CH$_2$-cyclohexyl)-C(=O)-NH-CH(CH$_2$-cyclohexyl)-C(=O)-RK-NH$_2$} | >200 |
| 18 | 30 | (indol-3-yl)-CH$_2$-C(=O)-{NH-CH(CH$_2$-cyclohexyl)-C(=O)-NH-CH(CH$_2$-cyclohexyl)-C(=O)-RK-NH$_2$} | 20 |
| 18 | 31 | (1,2,3,4-tetrahydronaphthalen-2-yl)-C(=O)-{NH-CH(CH$_2$-cyclohexyl)-C(=O)-NH-CH(CH$_2$-cyclohexyl)-C(=O)-RK-NH$_2$} | >200 |
| 18 | 32 | isoquinoline-3-C(=O)-{NH-CH(CH$_2$-cyclohexyl)-C(=O)-NH-CH(CH$_2$-cyclohexyl)-C(=O)-RK-NH$_2$} | 15 |
| 18 | 33 | Ph-CH=CH-CH$_2$-{NH-CH(CH$_2$-cyclohexyl)-C(=O)-NH-CH(CH$_2$-cyclohexyl)-C(=O)-RK-NH$_2$} | 5 |

-continued

TEST RESULTS

| SEQ ID NO: | Compound No. | Structure | IC$_{50}$ ($\mu$M) |
|---|---|---|---|
| 18 | 34 | Ph-CH=C(Me)-CH$_2$-{NH-CH(Cyclohexyl)-C(O)-NH-CH(Cyclohexyl)-C(O)-RK-NH$_2$} | 15 |
| 18 | 35 | Ph-CH=C(Et)-CH$_2$-{NH-CH(Cyclohexyl)-C(O)-NH-CH(Cyclohexyl)-C(O)-RK-NH$_2$} | 20 |
| 18 | 36 | PhO-CH$_2$-C(Me)$_2$-{NH-CH(Cyclohexyl)-C(O)-NH-CH(Cyclohexyl)-C(O)-RK-NH$_2$} | 7.5 |
| 18 | 37 | Quinoxaline-2-C(O)-{NH-CH(Cyclohexyl)-C(O)-NH-CH(Cyclohexyl)-C(O)-RK-NH$_2$} | >100 |
| 18 | 38 | 2-Naphthyl-SO$_2$-{NH-CH(Cyclohexyl)-C(O)-NH-CH(Cyclohexyl)-C(O)-RK-NH$_2$} | 10 |
| 19 | 39 | (N-pentyl-tetrahydroisoquinoline-3-carbonyl)-{NH-CH(Cyclohexyl)-C(O)-NH-CH(Cyclohexyl)-C(O)}-(NMeArg)-Arg-NH$_2$ | 8 |

-continued

TEST RESULTS

| SEQ ID NO: | Compound No. | Structure | IC$_{50}$ ($\mu$M) |
|---|---|---|---|
| 20 | 40 | 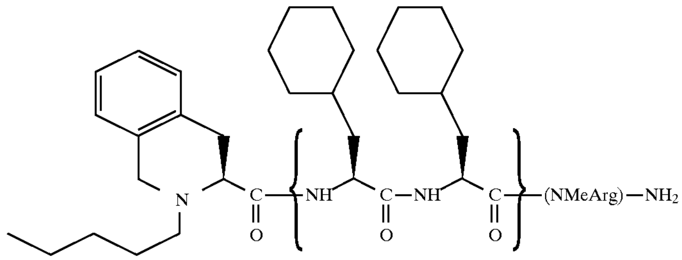 | 5 |
| 21 | 41 | 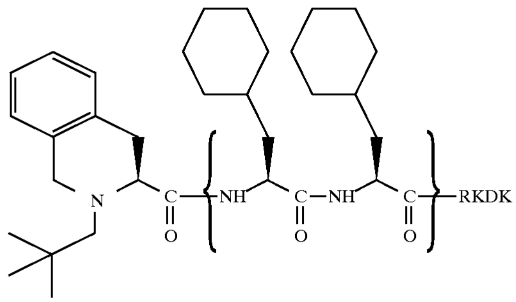 | 25 |
| — | 42 | | 2.0 |
| — | 43 | | 15 |
| — | 44 | | 5 |

TEST RESULTS

| SEQ ID NO: | Compound No. | Structure | IC$_{50}$ ($\mu$M) |
|---|---|---|---|
| — | 45 | 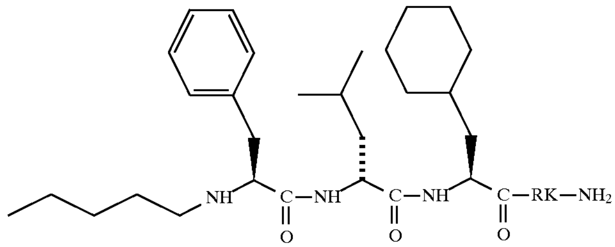 | 5 |
| 22 | 46 | 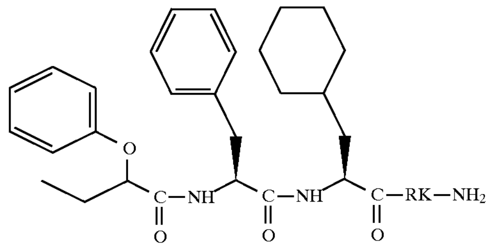 | 15 |
| 23 | 47 | 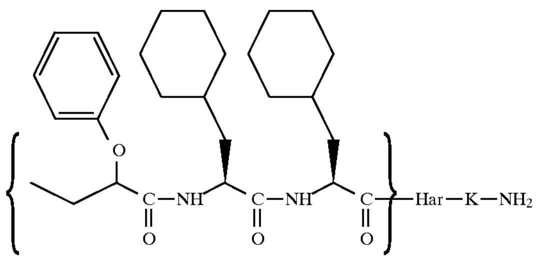 | 2.5 |
| 24 | 48 | 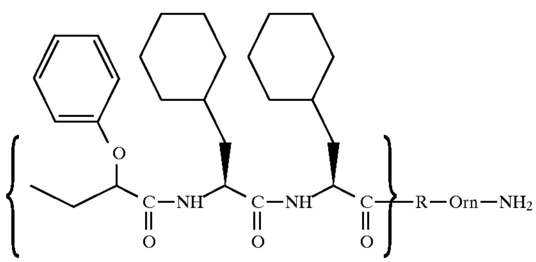 | 10 |
| 25 | 49 | 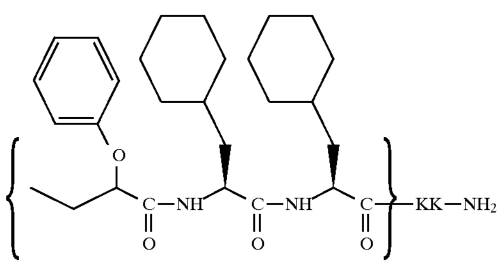 | 75 |
| 26 | 50 | 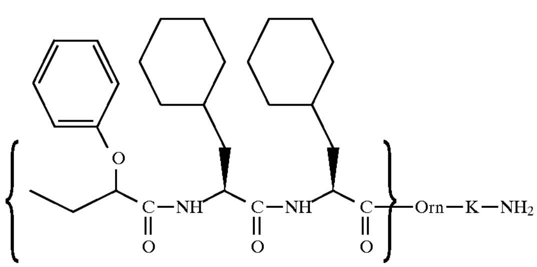 | 100 |

TEST RESULTS

| SEQ ID NO: | Compound No. | Structure | IC$_{50}$ ($\mu$M) |
|---|---|---|---|
| 27 | 51 | {PhO-CH(Et)-C(=O)-NH-CH(CH$_2$Cy)-C(=O)-NH-CH(CH$_2$Cy)-C(=O)-}RR-NH$_2$ | 2.5 |
| — | 52 | {PhO-CH(Et)-C(=O)-NH-CH(CH$_2$Cy)-C(=O)-NH-CH(CH$_2$Cy)-C(=O)-}R-(D-Lys)-NH$_2$ | 15 |
| 28 | 53 | {PhO-CH(Et)-C(=O)-NH-CH(CH$_2$Cy)-C(=O)-NH-CH(CH$_2$Cy)-C(=O)-}(N-MeArg)-Lys-NH$_2$ | 2.0 |
| 29 | 54 | {PhO-CH(Et)-C(=O)-NH-CH(CH$_2$Cy)-C(=O)-NH-CH(CH$_2$Cy)-C(=O)-}(N-MeArg)-Arg-NH$_2$ | 0.5 |
| 30 | 55 | {PhO-CH(Et)-C(=O)-NH-CH(CH$_2$Cy)-C(=O)-NH-CH(CH$_2$Cy)-C(=O)-}Har-Arg-NH$_2$ | 1.0 |
| — | 56 | PhO-(CH$_2$)$_3$-CH(CH$_2$Ph)-C(=O)-NH-CH(CH$_2$Cy)-C(=O)-RR-NH$_2$ | 6.0 |

TEST RESULTS

| SEQ ID NO: | Compound No. | Structure | IC$_{50}$ ($\mu$M) |
|---|---|---|---|
| 31 | 57 | 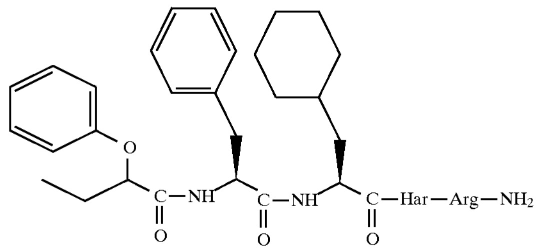 | 2.0 |
| — | 58 | | >100 |
| — | 59 | | 90 |
| — | 60 | | 25 |
| — | 61 | | |
| — | 62 | | |

TEST RESULTS

| SEQ ID NO: | Compound No. | Structure | IC$_{50}$ ($\mu$M) |
|---|---|---|---|
| — | 63 | 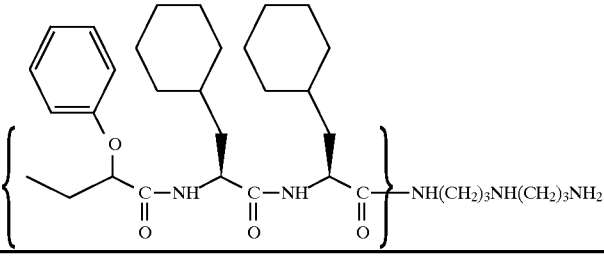 | |

Compounds 61–63 are also within the scope of the present invention, however, no test data was available at the time the application was filed.

The foregoing is offered primarily for purposes of illustration. It will be readily apparent to those skilled in the art that the structures, methods, composition components, synthesis and use conditions, and other parameters of the system described herein may be further modified or substituted in various ways without departing from the spirit and scope of the invention.

What is claimed is:

1. A compound of the formula:

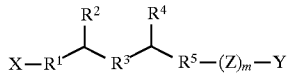 (I)

wherein:

$R^1$ and $R^3$ are members independently selected from the group consisting of CONH and isosteres thereof;

$R^2$ and $R^4$ are each cyclohexylmethyl;

$R^5$ is a member selected from the group consisting of $CH_2$, CO and SO;

X is a member selected from the group consisting of: arylalkyl, arylalkenyl, aryloxyalkyl, biphenyl, 1,2,3,4-tetrahydronaphthyl, quinolinyl, isoquinolinyl, 1,2,3,4-tetrahydroisoquinolinyl, 1,2,3,4-tetrahydroquinolinyl, N-alkyl 1,2,3,4-tetrahydroisoquinolinyl, N-alkyl 1,2,3,4-tetrahydroquinolinyl and N-(cycloalkyl)alkyl-1,2,3,4-tetrahydroisoquinolinyl, and radicals of the formula

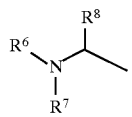

wherein:

$R^6$ and $R^7$ are members independently selected from the group consisting of H, $C_1$–$C_{10}$ alkyl, ($C_1$–$C_8$ cycloalkyl)-($C_1$–$C_4$ alkyl), ($C_1$–$C_{10}$ alkoxy)-($C_1$–$C_{10}$ alkyl), ($C_1$–$C_{10}$ alkylthio)-($C_1$–$C_{10}$ alkyl), aryl-($C_1$–$C_6$ alkyl), with the proviso that at least one of $R^6$ and $R^7$ is other than H, and $R^8$ is a benzyl or phenethyl;

Y is a member selected from the group consisting of $OR^9$ and $NR^{10}R^{11}$ wherein $R^9$, $R^{10}$ and $R^{11}$ are members independently selected from the group consisting of H, $C_1$–$C_{10}$ alkyl and a hydrocarbon radical substituted with an amine, guanidine, imidate, pyridine, imidazole, triazole or pyrimidine;

Z is a member selected from the group consisting of amino acids and peptides having from 2 to 20 amino acids; and m is zero or one (SEQ ID NO:32).

2. A compound of claim 1 wherein X is a member selected from the group consisting of arylalkyl, arylalkenyl, aryloxyalkyl, biphenyl, 1,2,3,4-tetrahydronaphthyl, quinolinyl, isoquinolinyl, 1,2,3,4-tetrahydroisoquinolinyl, 1,2,3,4-tetrahydroquinolinyl, N-alkyl 1,2,3,4-tetrahydroisoquinolinyl, N-(cycloalkyl)alkyl 1,2,3,4-tetrahydroisoquinolinyl, and N-alkyl 1,2,3,4-tetrahydroquinolinyl.

3. A compound of claim 1 wherein X is arylalkenyl.

4. A compound of claim 1 wherein X is 1-phenyloct-1-en-2-yl.

5. A compound of claim 1 wherein X is aryloxyalkyl.

6. A compound of claim 1 wherein X is 1-phenoxy-1-propyl.

7. A compound of claim 1 wherein X is 1-(2-naphthyloxy)-1-heptyl.

8. A compound of claim 1 wherein X is 1-phenoxy-1-pentyl.

9. A compound of claim 1 wherein X is 1-(1-naphthyloxy)-1-pentyl.

10. A compound of claim 1 wherein X is biphenyl.

11. A compound of claim 1 wherein X is 1,2,3,4-tetrahydronaphth-2-yl.

12. A compound of claim 1 wherein X is 2- or 3-quinolinyl.

13. A compound of claim 1 wherein X is N-alkyl 1,2,3,4-tetrahydroisoquinolinyl.

14. A compound of claim 1 wherein X is N-pentyl-1,2,3,4-tetrahydroisoquinolinyl.

15. A compound of claim 1 wherein X is a radical of the formula

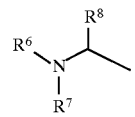

wherein:

$R^6$ and $R^7$ are members independently selected from the group consisting of H, $C_1$–$C_{10}$ alkyl, ($C_1$–$C_8$ cycloalkyl)-($C_1$–$C_4$ alkyl), ($C_1$–$C_{10}$ alkoxy)-($C_1$–$C_{10}$ alkyl), ($C_1$–$C_{10}$ alkylthio)-($C_1$–$C_{10}$ alkyl), aryl-($C_1$–$C_6$ alkyl), with the proviso that at least one of $R^6$ and $R^7$ is other than H; and $R^8$ is a benzyl or phenethyl.

16. A compound of claim 15 wherein $R^8$ is benzyl.

17. A compound of claim 15 wherein $R^8$ is phenethyl.

18. A compound of claim 15 wherein $R^6$ is H and $R^7$ is a member selected from the group consisting of $C_1$–$C_{10}$ alkyl, ($C_1$–$C_8$ cycloalkyl)-($C_1$–$C_4$ alkyl), ($C_1$–$C_{10}$ alkoxy)-($C_1$–$C_{10}$ alkyl), ($C_1$–$C_{10}$ alkylthio)-($C_1$–$C_{10}$ alkyl) and aryl-($C_1$–$C_6$ alkyl).

19. A compound of claim 15 wherein $R^6$ is H and $R^7$ is $C_1$–$C_{10}$ alkyl.

20. A compound of claim 15 wherein $R^6$ is H and $R^7$ is ($C_1$–$C_8$ cycloalkyl)-($C_1$–$C_4$ alkyl).

21. A compound of claim 15 wherein $R^6$ is H and $R^7$ is ($C_1$–$C_{10}$ alkylthio)-($C_1$–$C_{10}$ alkyl).

22. A compound of claim 15 wherein $R^6$ is H and $R^7$ is aryl-($C_1$–$C_6$ alkyl).

23. A compound of claim 15 wherein $R^6$ and $R^7$ are both $C_1$–$C_{10}$ alkyl.

24. A compound of claim 1 wherein $R^1$ and $R^3$ are independently CONH or isosteres thereof selected from the group consisting of —$CH_2NH$—, —$CH_2CH_2$—, —$CH_2S$—, —$CH_2SO$—, —$COCH_2$—, —$CH(OH)CH_2$—, —NHCO—, —$SO_2NH$—, —$CH_2O$—, —CH=CH— and 1,5-substituted tetrazole.

25. A compound of claim 1 wherein $R^1$ is —$CH_2NH$— and $R^3$ is CONH.

26. A compound of claim 1 wherein $R^5$ is CO.

27. A compound of claim 1 wherein $R^5$ is $CH_2$.

28. A compound of claim 1 wherein Z is a peptide of the formula $(AA^i)_n$ wherein AA represents an amino acid residue; i is an integer denoting the position downstream from $R^5$; and n is an integer of from 2 to 20; such that amino acid residues at any said position may be the same as or different from amino acid residues at any other said position (SEQ ID NO:32).

29. A compound of claim 28 wherein:

$AA^1$ is an amino acid selected from the group consisting of Arg, Har, Orn, Lys, Nε,Nε-Dimethyl-Lys, Nε-Acetimidyl-Lys, Nε-Phenylimidyl-Lys, Gln and Asn; and n is 2 to 10 (SEQ ID NO:33).

30. A compound of claim 28 wherein:

AA¹ is an amino acid selected from the group consisting of Arg, Har, Orn, Lys, Nε,Nε-Dimethyl-Lys, Nε-Acetimidyl-Lys, Nε-Phenylimidyl-Lys, Gln and Asn;

AA² is an amino acid selected from the group consisting of Asn, Gln, Arg, Lys, Har, Orn, Nε,Nε-Dimethyl-Lys and Nε-Methyl-Lys; and n is 2 to 10 (SEQ ID NO:34).

31. A compound of claim 28 wherein:

AA¹ is an amino acid selected from the group consisting of Arg, Har, Orn, Lys, Nε,Nε-Dimethyl-Lys, Nε-Acetimidyl-Lys, Nε-Phenylimidyl-Lys, Gln and Asn;

AA² is an amino acid selected from the group consisting of Asn, Gln, Arg, Lys, Har, Orn, Nε,Nε-Dimethyl-Lys and Nε-Methyl-Lys;

AA³ is an amino acid selected from the group consisting of Pro, Sar, Gly, Asp and Glu; and n is 3 to 10 (SEQ ID NO:35).

32. A compound of claim 28 wherein:

AA¹ is an amino acid selected from the group consisting of Arg, Har, Orn, Lys, Nε,Nε-Dimethyl-Lys, Nε-Acetimidyl-Lys, Nε-Phenylimidyl-Lys, Gln and Asn;

AA² is an amino acid selected from the group consisting of Asn, Gln, Arg, Lys, Har, Orn, Nε,Nε-Dimethyl-Lys and Nε-Methyl-Lys;

AA³ is an amino acid selected from the group consisting of Pro, Sar, Gly, Asp and Glu;

AA⁴ is an amino acid selected from the group consisting of Asn, Gln, Gly and Ala; and n is 4 to 10 (SEQ ID NO:36).

33. A compound of claim 28 wherein:

AA¹ is an amino acid selected from the group consisting of Arg, Har, Orn, Lys, Nε,Nε-Dimethyl-Lys, Nε-Acetimidyl-Lys, Nε-Phenylimidyl-Lys, Gln and Asn;

AA² is an amino acid selected from the group consisting of Asn, Gln, Arg, Lys, Har, Orn, Nε,Nε-Dimethyl-Lys and Nε-Methyl-Lys;

AA³ is an amino acid selected from the group consisting of Pro, Sar, Gly, Asp and Glu;

AA⁴ is an amino acid selected from the group consisting of Asn, Gln, Gly and Ala;

AA⁵ is an amino acid selected from the group consisting of Asp and Glu; and n is 5 to 10 (SEQ ID NO:37).

34. A compound of claim 28 wherein:

AA¹ is an amino acid selected from the group consisting of Arg, Har, Orn, Lys, Nε,Nε-Dimethyl-Lys, Nε-Acetimidyl-Lys, Nε-Phenylimidyl-Lys, Gln and Asn;

AA² is an amino acid selected from the group consisting of Asn, Gln, Arg, Lys, Har, Orn, Nε,Nε-Dimethyl-Lys and Nε-Methyl-Lys;

AA³ is an amino acid selected from the group consisting of Pro, Sar, Gly, Asp and Glu;

AA⁴ is an amino acid selected from the group consisting of Asn, Gln, Gly and Ala;

AA⁵ is an amino acid selected from the group consisting of Asp and Glu;

AA⁶ is an amino acid selected from the group consisting of Lys, Arg, Orn and Har; and n is 6 to 10 (SEQ ID NO:38).

35. A compound of claim 34 wherein:

AA¹ is Arg; and n is 2 to 6 (SEQ ID NO:39).

36. A compound of claim 34 wherein:

AA¹ is Arg;

AA² is Lys; and n is 2 to 6 (SEQ ID NO:40).

37. A compound of claim 34 wherein:

AA¹ is Arg;

AA² is Lys;

AA³ is Pro; and n is 3 to 6 (SEQ ID NO:41).

38. A compound of claim 34 wherein:

AA¹ is Arg;

AA² is Lys;

AA³ is Pro;

AA⁴ is Asn; and n is 4 to 6 (SEQ ID NO:42).

39. A compound of claim 34 wherein:

AA¹ is Arg;

AA² is Lys;

AA³ is Pro;

AA⁴ is Asn;

AA⁵ is Asp; and n is 5 to 6 (SEQ ID NO:43).

40. A compound of claim 34 wherein:

AA¹ is Arg;

AA² is Lys;

AA³ is Pro;

AA⁴ is Asn;

AA⁵ is Asp;

AA⁶ is Lys; and n is 6 (SEQ ID NO:44).

41. A compound of claim 1 wherein Y is NR¹⁰R¹¹, in which R¹⁰ and R¹¹ are members independently selected from the group consisting of H and C₁–C₁₀ alkyl.

42. A compound of claim 1 wherein Y is NR¹⁰R¹¹, in which R¹⁰ and R¹¹ are members independently selected from the group consisting of H and C₁–C₄ alkyl.

43. A compound of claim 1 wherein Y is NH₂.

44. A compound of claim 1 wherein m is zero and Y is NR¹⁰R¹¹ in which R¹⁰ and R¹¹ are members independently selected from the group consisting of H, C₁–C₁₀ alkyl and a hydrocarbon radical substituted with an amine, guanidine, imidate, pyridine, imidazole, triazole or pyrimidine.

45. A compound of claim 1 wherein:

R¹ and R³ are each CONH;

R² and R⁴ are each cyclohexylmethyl;

R⁵ is CO;

X is a radical of the formula

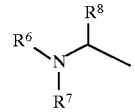

wherein R⁶ is H, R⁷ is C₁–C₁₀ alkyl, and R⁸ is benzyl;

Z is a peptide selected from the group consisting of ArgLys and ArgLysProAsnAspLys (SEQ ID NO:44); and Y is $NH_2$.

46. A compound of claim 1 wherein:
$R^1$ and $R^3$ are each CONH;
$R^2$ and $R^4$ are each cyclohexylmethyl;
$R^5$ is CO;
X is a radical of the formula

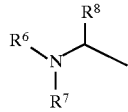

wherein $R^6$ is H, $R^7$ is pentyl, and $R^8$ is benzyl;
Z is a member selected from the group consisting of ArgLys and ArgLysProAsnAspLys (SEQ ID NO:44); and
Y is $NH_2$.

47. A compound of claim 1 wherein:
X is a member selected from the group consisting of arylalkenyl, aryloxyalkyl, biphenyl, 1,2,3,4-tetrahydronaphthyl, quinolinyl, isoquinolinyl, 1,2,3,4-tetrahydroisoquinolinyl, 1,2,3,4-tetrahydroquinolinyl, N-alkyl 1,2,3,4-tetrahydroisoquinolinyl, N-(cycloalkyl)alkyl 1,2,3,4-tetrahydroisoquinolinyl, N-alkyl 1,2,3,4-tetrahydroquinolinyl;
$R^1$ and $R^3$ are each CONH;
$R^2$ and $R^4$ are each cyclohexylmethyl;
$R^5$ is CO;
Z is a member selected from the group consisting of ArgLys and ArgLysProAsnAspLys (SEQ ID NO:44); and
Y is $NH_2$.

48. A compound of claim 47 wherein X is N-alkyl 1,2,3,4-tetrahydroisoquinolinyl.

49. A compound of claim 47 wherein X is N-pentyl-1,2,3,4-tetrahydroisoquinolin-3-yl.

* * * * *